United States Patent
Chen et al.

(10) Patent No.: US 11,215,594 B2
(45) Date of Patent: Jan. 4, 2022

(54) LOW POWER CIRCUITRY FOR BIASING A MULTI-CHANNEL GAS SENSOR ARRAY AND TO ACT AS A TRANSDUCER FOR A DIGITAL BACK-END

(71) Applicant: AerNos, Inc., San Diego, CA (US)

(72) Inventors: Albert Chen, Poway, CA (US); Sundip R. Doshi, San Diego, CA (US)

(73) Assignee: AERNOS, INC., San Diego, CA (US)

( * ) Notice: Subject to any disclaimer, the term of this patent is extended or adjusted under 35 U.S.C. 154(b) by 272 days.

(21) Appl. No.: 16/548,788

(22) Filed: Aug. 22, 2019

(65) Prior Publication Data
US 2020/0064321 A1  Feb. 27, 2020

Related U.S. Application Data

(60) Provisional application No. 62/721,289, filed on Aug. 22, 2018, provisional application No. 62/721,293, (Continued)

(51) Int. Cl.
*G01N 33/00* (2006.01)
*G01N 27/22* (2006.01)
(Continued)

(52) U.S. Cl.
CPC ........ *G01N 33/0031* (2013.01); *B01J 21/185* (2013.01); *B01J 23/00* (2013.01);
(Continued)

(58) Field of Classification Search
CPC ........ G01N 27/00; G01N 27/02; G01N 27/04; G01N 27/225; G01N 27/227; G01N 27/4076; G01N 27/045; G01N 33/00; G01N 33/0004; G01N 33/0009; G01N 33/0011; G01N 33/0022; G01N 33/0027; G01N 33/0031; G05B 2219/25127; G05B 2219/2525
See application file for complete search history.

(56) References Cited

U.S. PATENT DOCUMENTS

| 3,610,953 A | 10/1971 | Gordon et al. |
| 4,542,640 A | 9/1985 | Clifford |

(Continued)

FOREIGN PATENT DOCUMENTS

| GB | 2533294 A | 6/2016 |
| JP | 2012-511714 A | 5/2012 |
| WO | 2016145300 A1 | 9/2016 |

OTHER PUBLICATIONS

Ajeet Kaushik et al., "Organic-Inorganic Hybrid Nanocomposite-Based Gas Sensors for Enfironmental Monitoring", 2015, Chem Ref. 115,11,4571-4606 (Year: 2015).
(Continued)

*Primary Examiner* — Herbert K Roberts
*Assistant Examiner* — Fatemeh Esfandiari Nia
(74) *Attorney, Agent, or Firm* — Procopio, Cory, Hargreaves & Savitch LLP

(57) ABSTRACT

A nanomaterial-based gas sensor system comprising a low voltage circuitry which includes a transducer to detect changes in electrical properties of a multi-channel gas sensor array, analog signal conditioning, and an A/D conversion to provide a signal to a digital back-end.

19 Claims, 23 Drawing Sheets

Related U.S. Application Data filed on Aug. 22, 2018, provisional application No. 62/721,296, filed on Aug. 22, 2018, provisional application No. 62/721,302, filed on Aug. 22, 2018, provisional application No. 62/721,306, filed on Aug. 22, 2018, provisional application No. 62/721,309, filed on Aug. 22, 2018, provisional application No. 62/721,311, filed on Aug. 22, 2018, provisional application No. 62/799,466, filed on Jan. 31, 2019.

(51) Int. Cl.

| | |
|---|---|
| G01N 27/12 | (2006.01) |
| G01N 27/04 | (2006.01) |
| G05B 19/042 | (2006.01) |
| G01N 27/407 | (2006.01) |
| B01J 21/18 | (2006.01) |
| B01J 31/16 | (2006.01) |
| B01J 23/00 | (2006.01) |
| B82Y 30/00 | (2011.01) |
| B82Y 40/00 | (2011.01) |

(52) U.S. Cl.
CPC ........ *B01J 31/1691* (2013.01); *G01N 27/046* (2013.01); *G01N 27/121* (2013.01); *G01N 27/122* (2013.01); *G01N 27/125* (2013.01); *G01N 27/127* (2013.01); *G01N 27/128* (2013.01); *G01N 27/226* (2013.01); *G01N 27/227* (2013.01); *G01N 27/228* (2013.01); *G01N 27/4075* (2013.01); *G01N 33/004* (2013.01); *G01N 33/0011* (2013.01); *G01N 33/0022* (2013.01); *G01N 33/0037* (2013.01); *G01N 33/0042* (2013.01); *G01N 33/0047* (2013.01); *G05B 19/042* (2013.01); *B82Y 30/00* (2013.01); *B82Y 40/00* (2013.01); *G05B 2219/25127* (2013.01); *G05B 2219/25257* (2013.01)

(56) References Cited

U.S. PATENT DOCUMENTS

| | | | |
|---|---|---|---|
| 4,736,433 A * | 4/1988 | Dolby | .................... H03G 9/005 381/106 |
| 8,580,104 B2 | 11/2013 | Unwin et al. | |
| 9,612,993 B2 | 4/2017 | Field et al. | |
| 9,696,311 B2 | 7/2017 | Haick et al. | |
| 2010/0147684 A1 | 6/2010 | Park et al. | |
| 2010/0323925 A1 | 12/2010 | Gabriel et al. | |
| 2012/0133422 A1 | 5/2012 | Silva, Jr. et al. | |
| 2012/0265474 A1 | 10/2012 | Rearick et al. | |
| 2013/0062211 A1 | 3/2013 | Deshusses et al. | |
| 2013/0075794 A1* | 3/2013 | Bradley | .............. H01L 29/0673 257/253 |
| 2015/0268207 A1 | 9/2015 | Motayed et al. | |
| 2015/0323510 A1 | 11/2015 | Huynh et al. | |
| 2015/0378954 A1 | 12/2015 | Field | |
| 2016/0238553 A1 | 8/2016 | Shachar | |
| 2017/0350936 A1 | 12/2017 | McMeen et al. | |
| 2018/0003660 A1 | 1/2018 | Tayebi et al. | |
| 2018/0284737 A1* | 10/2018 | Celia | .................. G05B 23/0294 |
| 2019/0025237 A1 | 1/2019 | Kelly et al. | |
| 2019/0250135 A1 | 8/2019 | Andersson et al. | |
| 2020/0064321 A1 | 2/2020 | Chen et al. | |
| 2020/0256840 A1 | 8/2020 | Doshi et al. | |

OTHER PUBLICATIONS

International Search Report and Written Opinion for PCT International Applicaton No. PCT/US2019/047791, dated Dec. 5, 2019, 13 pages.

Brust, Mathias et al., "Synthesis of Thiol-derivatised Gold Nanoparticles in a Two-Phase Liquid-Liquid System", 1994, J Chem Soc Chem Commun, 7:801-802 (Year: 1994).

Brust, Mathias et al., Synthesis of Thiol-derivatized Gold Nanoparticles in a Two-Phase Liquid-Liquid System, 1994, J Chem Soc Chem Commun, 7:801-802 (Year: 1994).

Zhang et al., A Rapid Room-Temperature NO2 Sensor Based on Tellerium-SWNT Hybrid Nanostrutures, 2012, J. Phys.Chem, C., 116, 20067-20074 (Year: 2012).

Jung et al., Enhanced Humidity-sensing response of metal oxide coated carbon nanotube, 2015, Sensors and Actuators A, 223, 11-17 (Year: 2015).

Sofian M. Kanan, et al. Semiconducting Metal Oxide Based Sensors for Selective Gas Pollutant Detection, Oct. 2009, Sensors 9(10), 8158-8196 (Year: 2009).

Su et al., Metal nanoparticles and DNA co-functionalized single-walled carbon nanotube gas sensors, 2013, Nanotechnology, 24 (Year:2013).

Su, Single Walled Carbon Nanotube Based Hybrid Nanostructure Gas Sensor Array for Air Quality Index, 2014, pp. 6-36 (Year: 2014).

Syed Mubeen et al., "Hybrid tin-oxide-SWNT nanostructures based gas sensor", Mar. 2013, Electrochimica Acta, 92, p. 484-490 (Year: 2013).

Chen, Yin-sheng, et al., "Fault detection, isolation, and diagnosis of status self-validating gas sensor arrays "Review of Scientific Instruments 87.4 (2016): 045001. (Year: 2016).

Murali, Pramod, et al. A CMOS gas sensor array platform with Fourier transform based impedance spectroscopy. 'IEEE Transactions on Circuits and Systems I: Regular Papers 59.11 (2012): 2507-2517 (Year: 2012).

Virji, Shabnam et al., "Polyaniline nanofibre gas sensors: examination of response mechanisms "Nano letters 4.3 (2004): 491-496. (Year: 2004).

Li, Haitao, et al. "Low power multimode electrochemical gas sensor array system for wearable health and safety monitoring." IEEE Sensors Journal 14.10 (201): 3391-3399. (Year: 2014).

\* cited by examiner

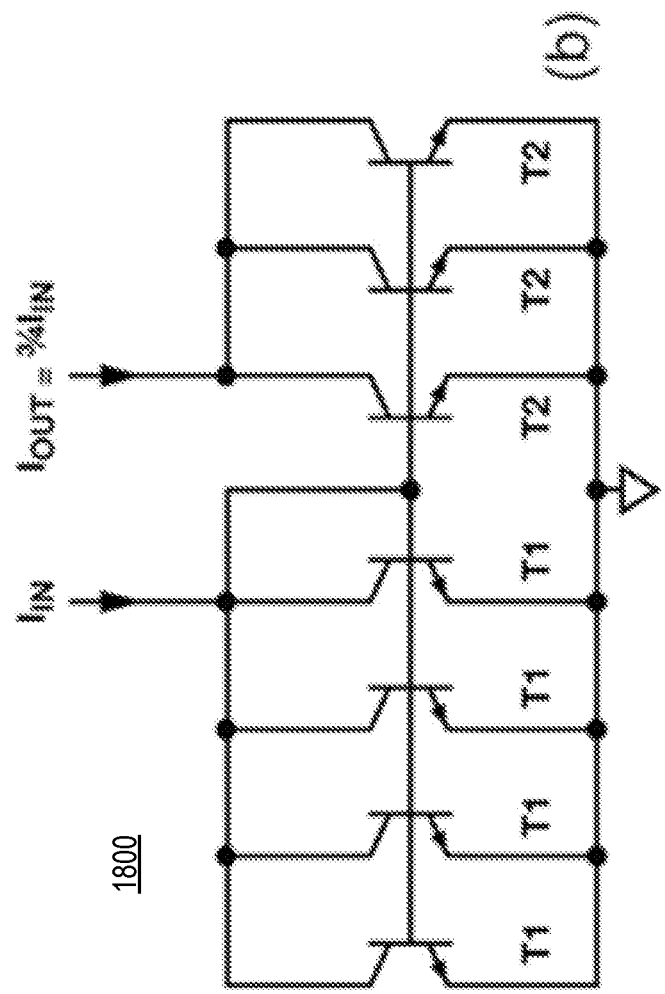
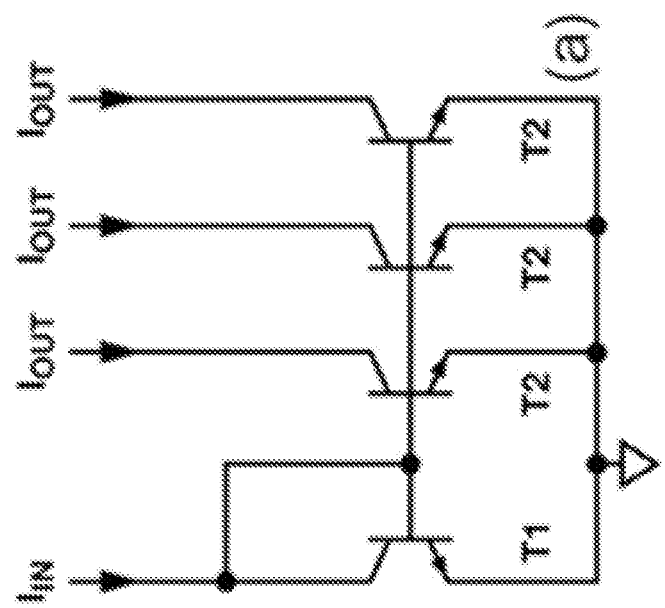
FIG. 18

LOW POWER CIRCUITRY FOR BIASING A MULTI-CHANNEL GAS SENSOR ARRAY AND TO ACT AS A TRANSDUCER FOR A DIGITAL BACK-END

CROSS-REFERENCE TO RELATED APPLICATIONS

This application claims priority to U.S. Provisional Patent Application No. 62/721,289, filed Aug. 22, 2018, U.S. Provisional Patent Application No. 62/721,293, filed Aug. 22, 2018, U.S. Provisional Patent Application No. 62/721,296, filed Aug. 22, 2018, U.S. Provisional Application No. 62/721,302, filed Aug. 22, 2018, U.S. Provisional Patent Application No. 62/721,306, filed Aug. 22, 2018, U.S. Provisional Patent Application No. 62/721,309, filed Aug. 22, 2018, U.S. Provisional Application No. 62/721,311, filed Aug. 22, 2018, U.S. Provisional Patent Application No. 62/799,466, filed Jan. 31, 2019, the contents of which are incorporated herein by reference.

BACKGROUND

1. Technical Field

The embodiments herein relate to a nano gas sensing system, and more particularly to an analog front-end for biasing and measuring of one or more gas sensors and conditioning and conversion of an analog signal(s) for an array of nanomaterial-based gas sensors for a digital back-end.

2. Related Art

Conventional digital gas sensor systems typically power and measure a single metal oxide sensor. Digital gas sensors are typically static in their sampling methodology, and in general, this involves sampling an ADC for converting the voltage to a digital value, at fixed intervals. This value is then converted back to a gas concentration, typically via a linear fit model.

Conventional techniques for measuring a gas sensor typically provide either a voltage or current source which may or may not be constant. The quantity being measured is turned into a voltage for conversion into a digital signal. In many applications there is a limited range of measurement, or a tradeoff between measurement range and accuracy. Other techniques that rely on an optical method of measurement and detection are often bulky and/or expensive.

In applications with multiple sensors, the measurement circuitry is duplicated and/or multiplexed. As the number of sensors increases, the delay between each sensor's measurement may lead to difficulty in capturing the true signal of interest.

Commercially available gas sensors can also be cumbersome to use, expensive and limited in performance (e.g. accuracy, selectivity, lowest detection limit, etc.). In addition, other major drawbacks may include inability to detect different types of gases at the same time, inability to measure absolute concentration of individual gases, the requirement for frequent re-calibration, a size incompatible with integration into small form factor systems such as wearable devices, the reliance on power-hungry techniques such as heating or on technologies not well suited to manufacturing in very high volume.

The ability to accurately detect multiple gases at the same time, often at parts-per-billion (PPB) sensitivity is becoming crucial to a growing number of industries as well as to the world-wide expansion of air quality monitoring initiatives aiming to address household and urban air pollution challenges.

SUMMARY

A nano gas sensor architecture that delivers key fundamental attributes required for the broad deployment of sensors capable of low detection limits (PPB) in support of highly granular collection of gas information in ambient air is described herein.

According to one aspect, a sensor system comprises a sensor array comprising a plurality of sensing elements, wherein each of the plurality of sensing elements are functionalized with a deposited mixture consisting of hybrid nanostructures and a molecular formulation specifically targeting at least one of a plurality of gases, and wherein each of the plurality of sensing elements comprises a resistance and a capacitance, and wherein at least one resistance and capacitance are altered when the interacting with gaseous chemical compounds; an analog front-end coupled with the sensor array and configured to detect the alteration in the resistance or capacitance and produce an analog signal indicative thereof, power each of a plurality of sensing channels associated with each the plurality of sensing elements, and convert the analog signal to a digital signal, the analog-front end comprising: an Analog-to-Digital (ADC), a parking circuit, and a measurement circuit; and a digital back end coupled with the analog-front end and configured to control the analog front-end, the digital backend comprising: memory comprising, algorithms, models and instructions.

These and other features, aspects, and embodiments are described below in the section entitled "Detailed Description."

BRIEF DESCRIPTION OF DRAWINGS

Features, aspects, and embodiments are described in conjunction with the attached drawings, in which:

FIG. 18 is a diagram illustrating an OP-AMP circuit that can be used in place of the current mirror of FIG. 15;

DETAILED DESCRIPTION

Figure 1:
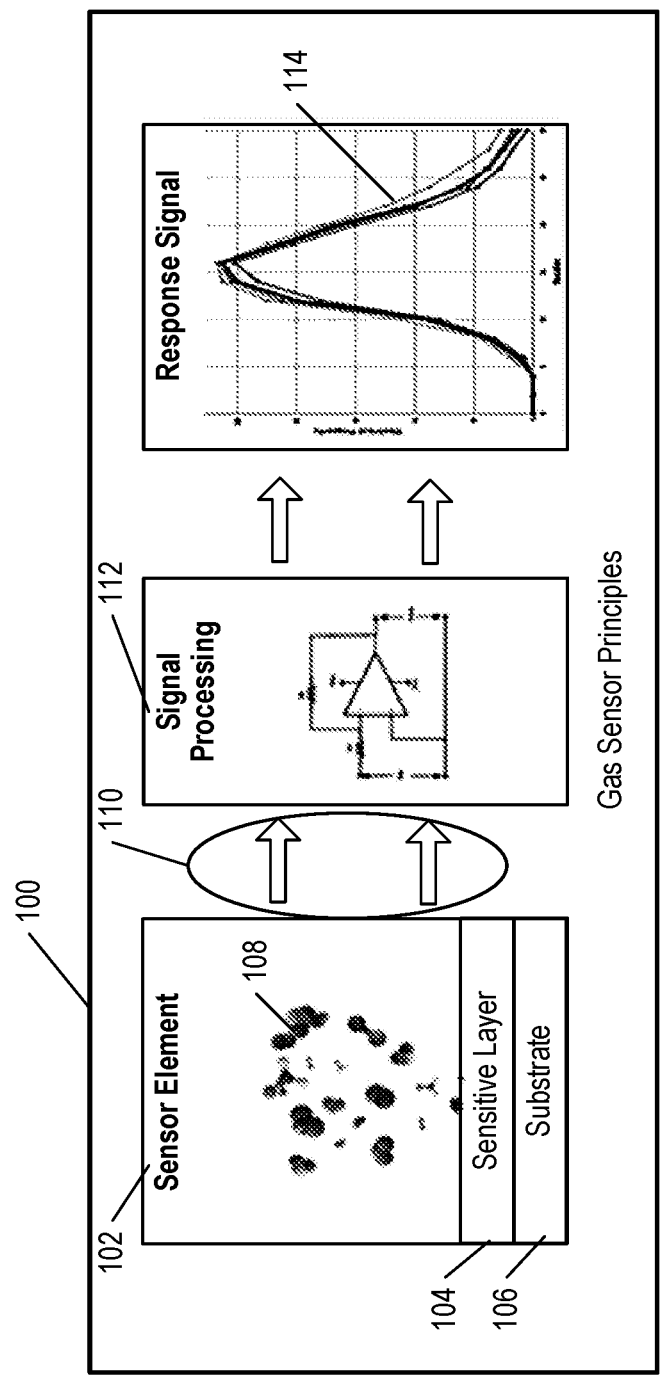
FIG. 1 illustrates the basic principles to construct a gas sensor.

Embodiments for a hybrid nanostructure gas sensing system are described herein. The disclosure and the various features and advantageous details thereof are explained more fully with reference to the non-limiting embodiments and examples that are described and/or illustrated in the accompanying drawings and detailed in the following. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure. Moreover, it is noted that like reference numerals represent similar parts throughout the several views of the drawings.

The architecture embodied in the hybrid nanostructure gas sensing system described herein achieves the basic requirement of selectively identifying the presence of a gas analyte in diverse mixtures of ambient air but it is also designed to identify multiple gases at the same time, to be compatible in terms of size and power with very small form factors (including for mobile and wearable applications), to be easy to Integrate in IoT applications and to be self-calibrating, thus unshakling the application and/or the service provider from the burden and expense of regular re-calibration.

FIG. 1 describes the basic ingredients for a successful gas sensor 100. As can be seen, such a sensor includes a sensing element 102 that is created by depositing a sensitive layer 104 over a substrate 106. The sensing element 102 can then interact with gaseous chemical compounds 108 altering one or more electrical properties of the sensing element 102. The change in electrical properties can be detected by feeding the sensor raw signals 110 through specially designed signal processing electronics 112. The resulting response signals 114 can be measured and quantified directly or through the application of pattern recognition techniques.

The embodiments described herein comprise six basic elements. The first is the basic sensor element or sensing channel, which combines a structural component, built on a substrate suitable for reliable high-volume manufacturing, with a deposited electrolyte containing hybrid nano structures in suspension. The formulation of the electrolyte is specific to a particular gas or family of gases. A silicon substrate 106 and the structural component can be built using a MEMS manufacturing process. The structural component is essentially an unfinished electrical circuit between two electrodes. The deposition of the electrolyte completes the electrical circuit and, when biased and exposed to gas analytes, changes to one or more of the electrical characteristics of the circuit are used to detect and measure gases.

The second element is the arrangement of multiple sensing channels into an array structure specifically designed and optimized to interface with data acquisition electronics 112. The array structure, combined with the use of pattern recognition algorithms, makes it possible to detect multiple gases at the same time with a single sensor by customizing one or more of the individual sensing channels in the array for a specific gas or family of gases while using other sensing channels to facilitate such critical functions as selectivity.

Figure 2:
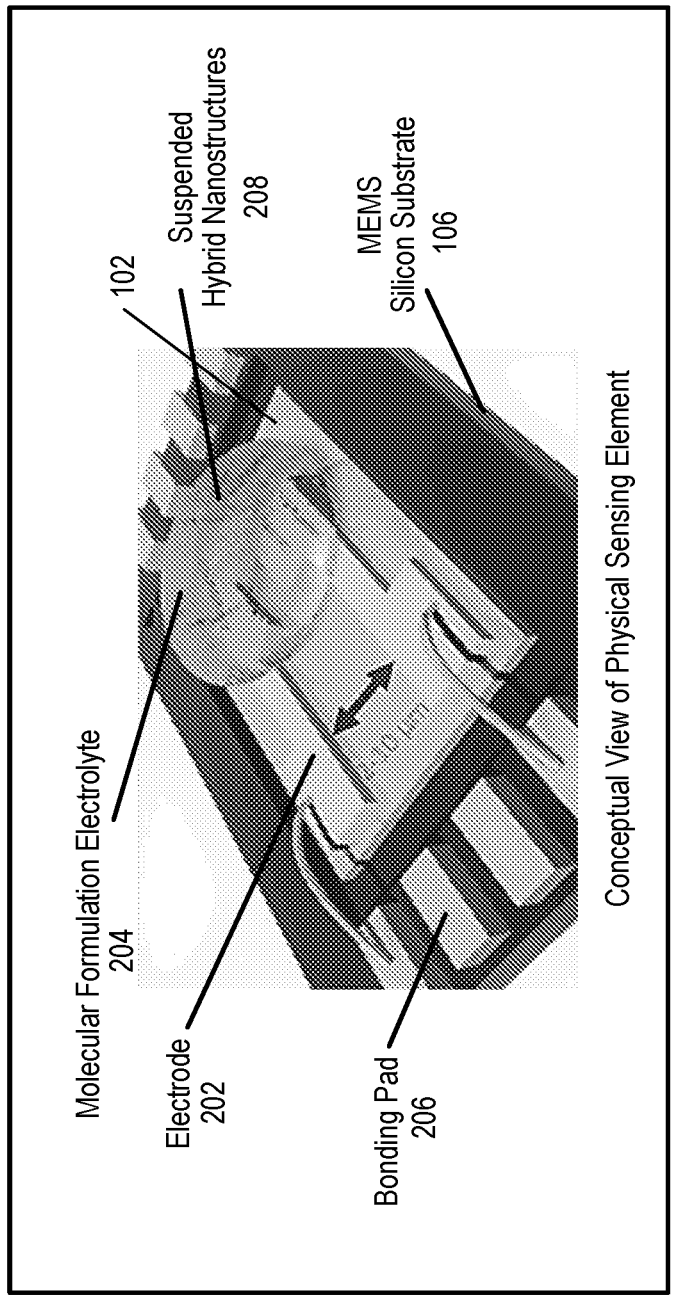
FIG. 2 is a prospective view of a physical implementation of a hybrid nanostructure gas sensing element in accordance with one embodiment.

FIG. 2 is a conceptual view of a hybrid nanostructure physical sensing element 102 in accordance with one example embodiment. Different materials can be used for the substrate 106 on which the rest of the sensing element 102 is constructed. But from the perspective of very high volume manufacturing, silicon technology can be preferred and specifically MEMS technology, which provides the necessary foundation for a customer-defined set of manufacturing steps with the flexibility to modulate the complexity of the process based on the sophistication of the sensor chip being built, e.g., to support further innovation or to address special product needs. Silicon technology also provides access to time-proven test methods and multiple sources of Automated Test Equipment that can be customized to fit the needs of gas sensing technology.

The sensing element 102 is made of an incomplete or "open" electrical circuit between two electrodes 202, which is then completed or "closed" by depositing, a molecular formulation electrolyte 204 with hybrid nanostructures 208 in suspension. The process is compatible with several commonly used deposition techniques but does require specially customized equipment and proprietary techniques to achieve the desired quality and reproducibility in a high-volume manufacturing environment. In certain embodiments, the sensing element 102 can be specially patterned to support efficient deposition of nanomaterial in pico-litter amounts and to facilitate incorporation of multiple elements into an array to enables the design of multi-gas sensors.

Electrodes 202 can then be bonded to bonding pads 206 in order to communicate signals 110 to the rest of the system.

One or more molecular formulations may be necessary to completely and selectively identify a particular gas. Combining multiple sensing elements 102, each capable of being "programmed" with a unique formulation, into a sensor array provides the flexibility necessary to detect and measure multiple gases at the same time. It also enables rich functional options such as for instance measuring humidity, an important factor to be accounted for in any gas sensor design, directly on the sensor chip (after all water vapor is just another gas). Another example is the combination for the same gas or family of gases of a formulation capable of very fast reaction to the presence of the gas while another formulation, slower acting, may be used for accurate concentration measurement; this would be important in applications where a very fast warning to the presence of a dangerous substance is required but actual accurate concentration measurement may not be needed at the same time (e.g. first responders in an industrial emergency situation).

Figure 3:
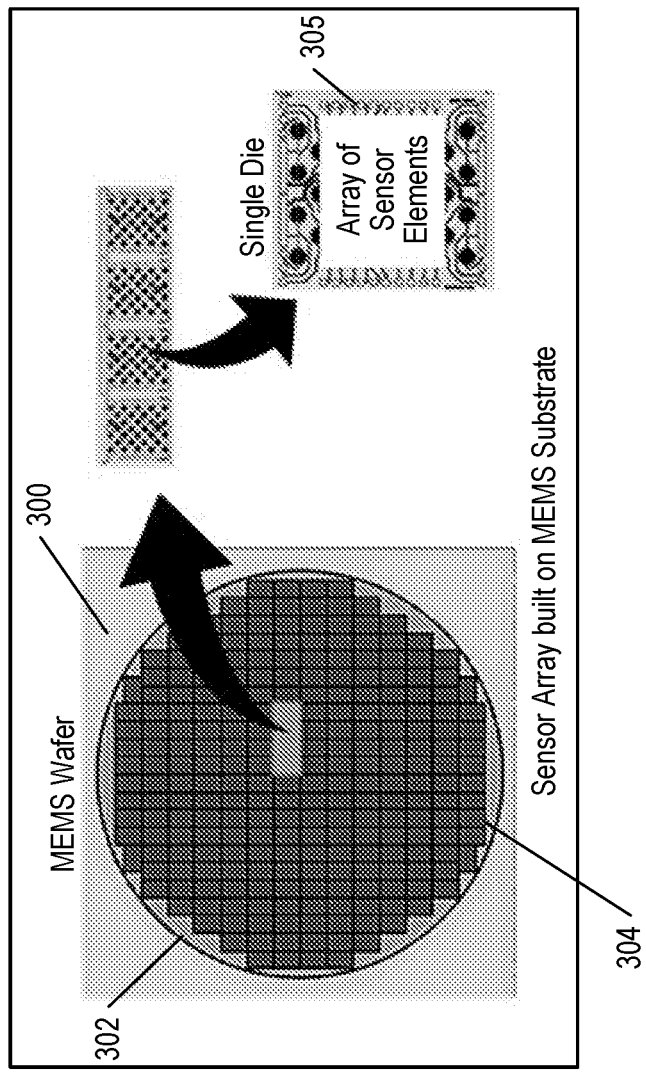
FIG. 3 is a diagram illustrating an embodiment of a gas sensor array.

FIG. 3 illustrates the preferred embodiment of a multi-channel, gas sensor array 305 where a silicon substrate 302 is used with a MEMS manufacturing process to build the structure of the sensing channels on which the molecular formulations 204 can be deposited. For illustration purposes the size of the individual sensor die 304 is shown as being much larger than achievable in practice; a single 8" wafer 300 will typically yield several thousand multi-gas capable sensor chips. An array 305 of sensing elements 102 is implemented on a single die 304 and each wafer 300 yields several thousand dies or chips 304. Each sensing element 102 can then be functionalized by depositing a specific molecular formulation 204 thereon.

Thus, after MEMS manufacturing, additional steps are required to complete the fabrication of each sensing element 102. First, molecular formulations 204 are deposited and cured using specialized equipment. This happens at wafer level and the equipment is designed in a modular fashion to allow for the scaling of the output of a manufacturing facility by duplicating modules and fabrication processes in a copy-exactly fashion. After completion of the manufacturing steps, the wafers 300 must be singulated using a clean dicing technology in order to prevent damage to the sensing elements 102. An example of such technology is Stealth dicing.

A channel 102 consists of two main elements: electrodes and a well. The electrodes, over which the formulation 204 is being deposited, form an open circuit until hybrid nano-material 208 creates a bridge between two adjacent electrodes. The well is a wall surrounding the electrodes. The well prevents the overflow of material during the formulation deposition process. The well is formed in two sections ("top" and "bottom"). A complete channel 102 therefore consists of a fixed number of electrode segments and two separate walls outside the top and bottom electrodes. Assuming a chip has 32 channels, a total of 3,300 chips form a complete 8-inch wafer.

Figure 8:
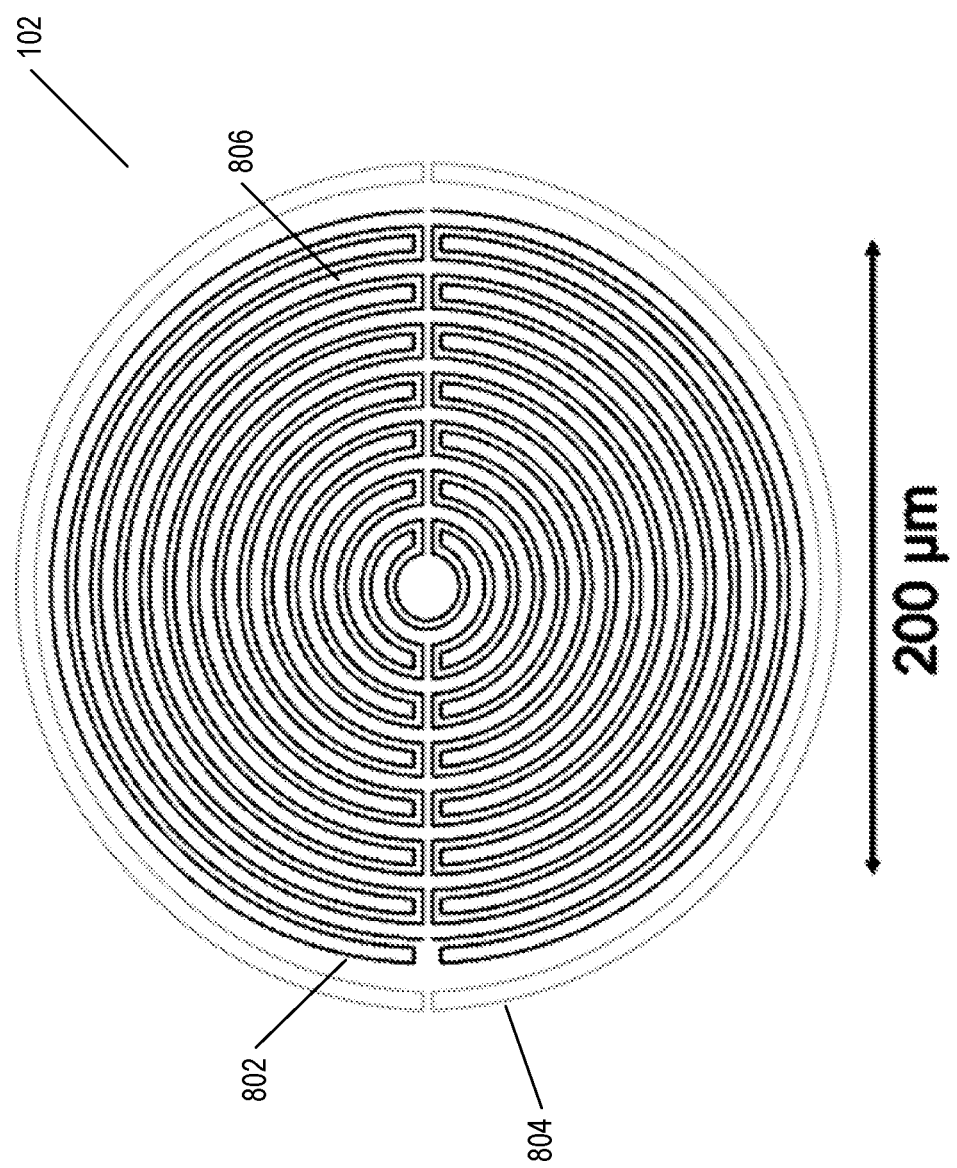
FIG. 8 is a diagram illustrating an example, single channel that can be replicated in the sensor array of FIG. 3 included in the sensor chip of FIGS. 3 and 4 in accordance with one embodiment.

FIG. 8 is diagram illustrating an example, single channel 102 in accordance with one embodiment. Each channel 102 consists of electrodes 802 and well 804. The electrodes 802 are on top of a Si/SiO$_2$ substrate 302 (not shown in FIG. 8). In certain embodiments the material of the substrate 302 is made of Silicon (Si), but the choice of substrate is not limited to Si. Other materials such as glass, aluminum oxide, a polyimide soft film, a printed circuit board (PCB), and a variety of paper supports can be chosen depending on the embodiment. A dielectric layer (not shown) included in the substrate can be made of Silicon Dioxide (SiO$_2$), but again the selection of material is not limited to SiO$_2$; For example, another option could be Silicon Nitride (Si$_3$N$_4$).

In certain embodiment, the thickness of the dielectric SiO$_2$ layer is 300 nm, but it can range from about 200 to 500 nm, including the following specific values: 200, 220, 230, 240, 250, 300, 350, 400, 450, and 500 nm. The thickness of the substrate 302, can be 500 µm but could range from about 250 to 750 µm, including the following specific values: 250, 300, 350, 400, 450, 500, 550, 600, 650, 700, and 750 µm. The width of a single channel 102 can be 200 µm but could range from about 100 to 600 µm, including the following specific values: 100, 150, 200, 250, 300, 350, 400, 450, 500, 550, and 600 µm.

In certain embodiments, the electrode 802 is built using Platinum (Pt) and Titanium (Ti) layers but the choice of material can include other metals such as Chromium (Cr) and Gold (Au). In certain embodiments, the total thickness of the Pt/Ti layer is 300 nm but could range from about 200 to 400 nm, including the following specific values: 200, 250, 300, 350, 400 nm. In certain embodiments, the shape of the electrode 802 is circular as shown. This specific shape was chosen for the following reasons: 1) create a homogeneous deposition form, 2) keep the material formulation within the electrodes for optimum sensor performance, 3) prevent the overflow of the deposited formulation, and 4) ensure fast drying of the deposited formulation; however, it will be understood that other shapes can be used in conjunction with the embodiments described herein.

In certain embodiments, the width of the electrode is 5 µm but could range from 3 to 10 µm, including the following specific values: 3, 4, 5, 6, 7, 8, 9, and 10 µm. In certain embodiments, the number of coils per electrode pair is 7 but could range from 7 to 14.

In certain embodiments, the well 804 has top and bottom sections with the two sections combining to create the full well 804 around the electrodes 802. The material for the well can be Si$_3$N$_4$ but other materials could also be used (e.g. a combination of SiO$_2$ and Si$_3$N$_4$). In certain embodiments, the well 804 is designed to 1) confine the formulation over the electrodes 802, 2) prevent cross-contaminations from an adjacent channel, and 3) provide an alignment key for volume deposition equipment.

The gap 806 between the electrodes 802 is where the sensing formulation 204 needs to be deposited. The deposited formulation 204 creates the connection necessary to complete the electrical circuit and ultimately becomes a sensitive layer for gas analytes in various applications. The circuit is open if a formulation 204 has not been deposited. In certain embodiments, the size of the gap is 3 µm, but the gap size could range from about 2.5 to 10 µm, including the following specific values: 2.5, 3, 3.5, 4, 4.5, 5, 5.5, 6, 6.5, 7, 7.5, 8, 8.5, 9, 9.5 and 10 µm.

Figure 9:
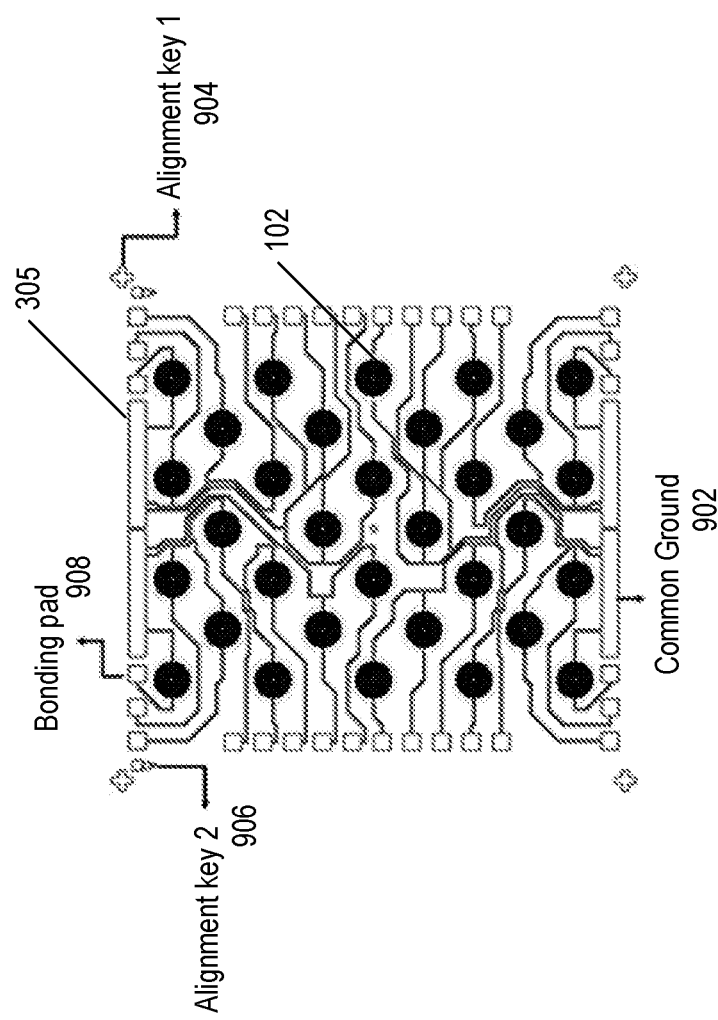
FIGS. 9 and 10 are diagrams illustrating example embodiments for a complete sensor chip of FIG. 3 comprising 32 channels.
Figure 10:
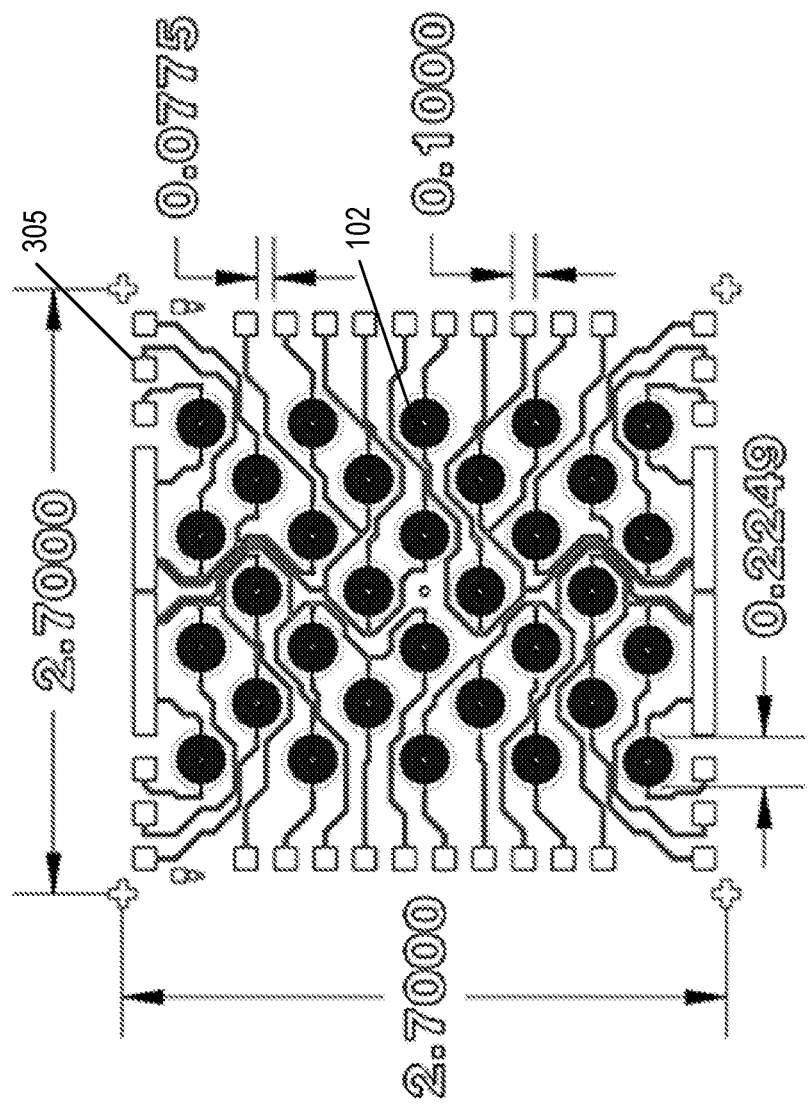

FIGS. 9 and 10 are diagrams illustrating example embodiments for a complete sensor chip 304 comprising 32 channels. In certain embodiments, each chip 304 is 2.7 mm×2.7 mm and has four, separate common ground 902 for reducing signal noise and to create redundancy to reduce the chance of chip malfunction. Alignment key 1 (904) is used for alignment during wafer dicing (die singulation). Alignment key 2 (906) is a special mark for precise alignment within the wafer for high volume manufacturing. By combining both alignment keys 1 and 2, very precise volume deposition can be achieved.

In certain embodiments, each chip 304 has 32 bonding pads 908 for wire bonding individual channels 102 to connect the on-chip circuitry to off-chip electronics. Every channel 102 can be an individual sensor for gas sensing purpose. As illustrated in FIG. 10, in certain embodiments, each pad 908 is 0.1 mm×0.1 mm and the spacing between two bonding pads 908 is 0.075 mm. Moreover, as illustrated, the overall chip 304 area can be about 2.7 mm×2.7 mm, and the diameter of each channel 102 can be approximately 0.225 mm. Still moreover, while the example of FIGS. 9 and 10 show a chip 305 with 32 channels, a variety of implementations are possible with 8, 16, 20, 24, 32, 36 or 40 channels, yielding a variety of chip area from 2 mm×2 mm to 5 mm×5 mm.

The number of deposited formulations 204 can vary depending on the target application. In certain embodiments with 32 channels, as many as 32 different formulations 204 could be deposited; however, it could be any number between 1 and 32. The spacing between each channel 102, from center to center, can be adjusted to fit various requirements and applications. In certain embodiments, the spacing is 600 μm but could range from 400 to 800 μm.

Figure 11:
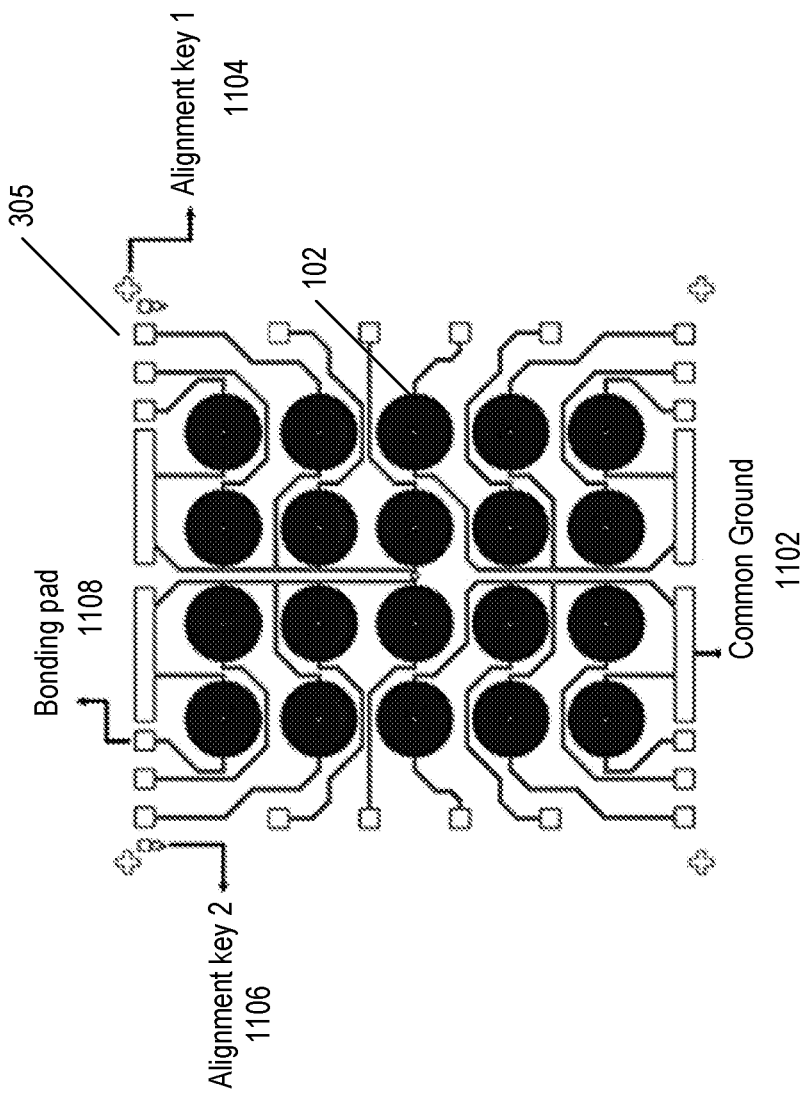
FIGS. 11 and 12 are diagrams illustrating another example embodiment for a complete sensor chip comprising 20 channels.
Figure 12:
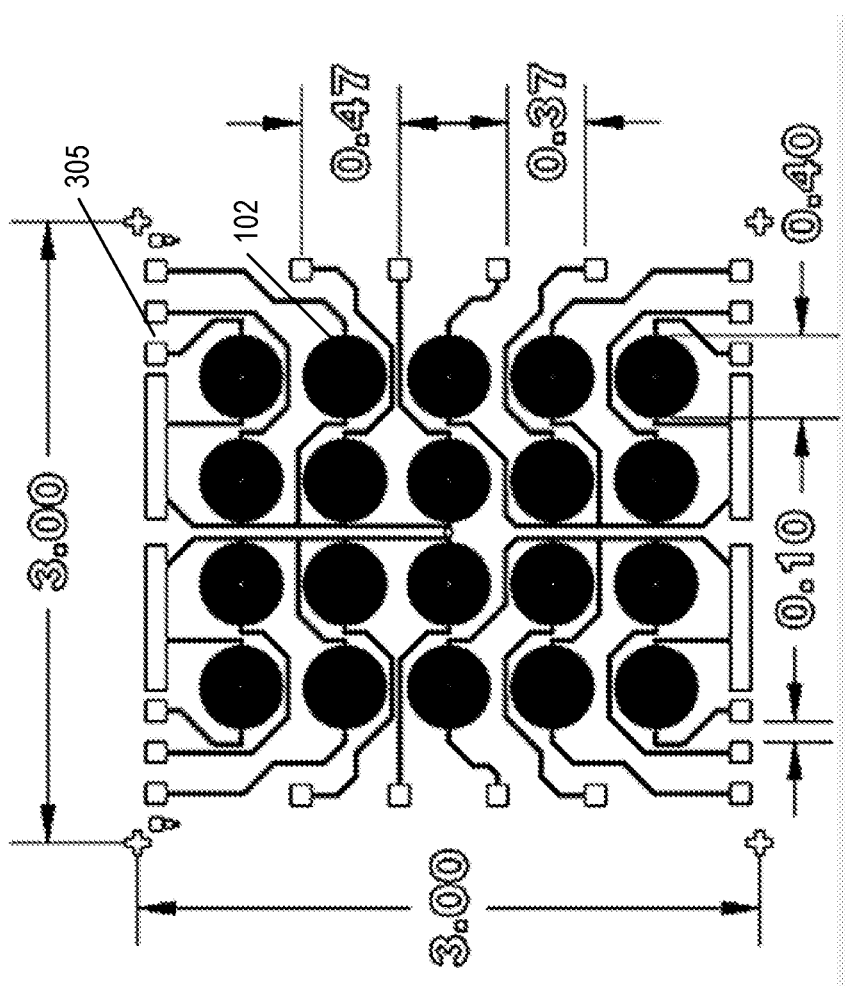

FIGS. 11 and 12 are diagrams illustrating another example embodiment for a complete sensor chip 304 comprising 20 channels 102. To adapt to a variety of applications, different numbers of channels 102 can be used. In this particular embodiment, each channel 102 is larger (400 μm) than in the 32-channel embodiment described in FIGS. 9 and 10. For certain applications, such as air quality monitoring or leak detection, to achieve the goal and retrieve useful information, the volume of deposited sensitive material 204 in each channel 102 may need to be more than a nano-liter. Moreover, in certain specific applications such as in-home environment monitoring, a larger channel size is critical to obtain a clean signal for precise measurement.

In embodiment of FIGS. 11 and 12, the chip 304 is 3 mm×3 mm in area. Each chip 304 has 20 individual bonding pads 1108 for signal read-out. Each pad is 0.1 mm×0.1 mm and the spacing between two bonding pads 1108 is 0.1 mm and 0.37 mm respectively, depending on the location of the pads 1108. Alignment keys 1 (1104) and 2 (1106) serve the same chip alignment purpose and provide the means for precise volume deposition.

Figure 13:
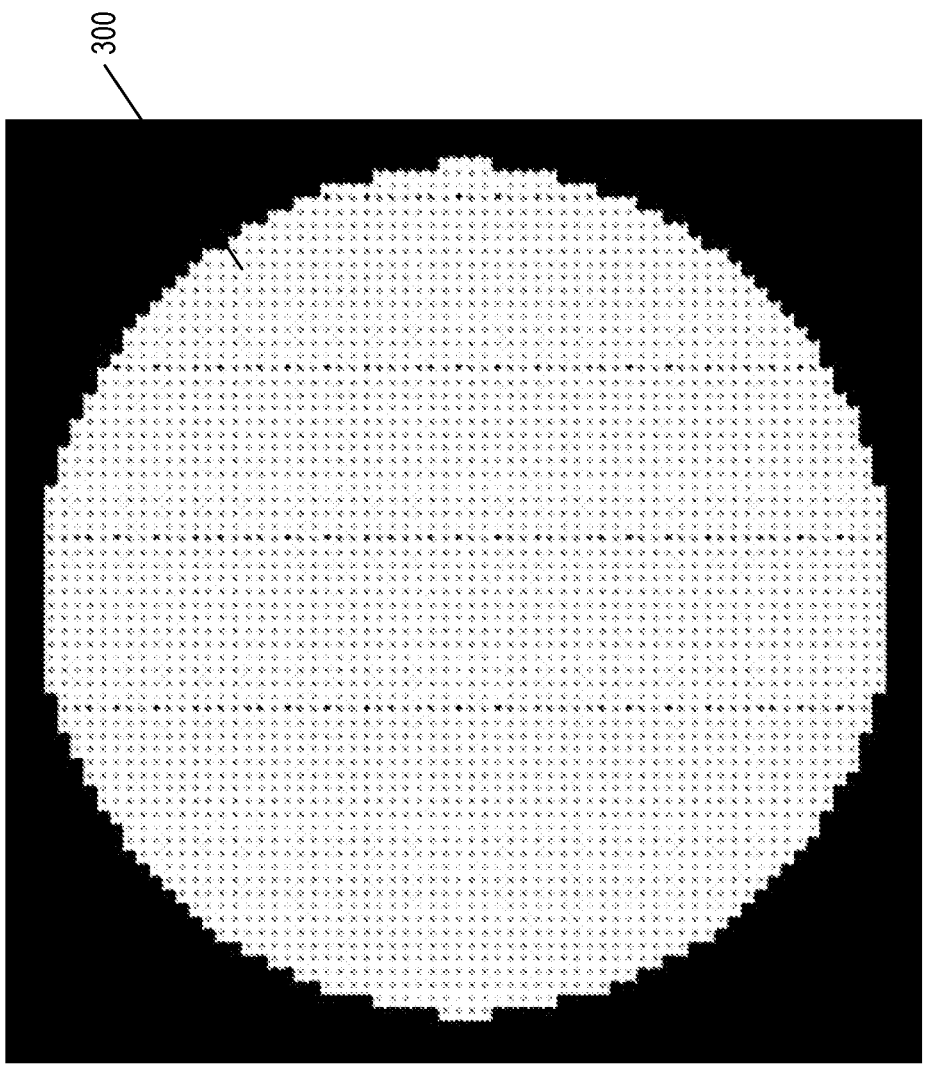
FIG. 13 is an illustration of a complete wafer implementing either embodiment described in FIGS. 5 through 7.

FIG. 13 is an illustration of a complete wafer 300 implementing either embodiment described in FIGS. 9 through 11. With a chip area of 3 mm×3 mm, an 8-inch wafer consists of approximately 3,300 chips. The spacing between each chip 304 is set for optimum dicing operation. The amount of chips 304 per wafer 300 has also been calculated to support high wafer processing yield.

The third element is the electronic transducer that detects changes in the electrical characteristics of the sensor array 305, provides signal conditioning and converts the analog signal from the sensor elements 102 into a digital form usable by the data acquisition system, described in more detail below. The transducer can be a low voltage analog circuit that provides biasing to the array of sensing channels 102 and two functional modes: parking and measurement. Sensing channels 102 are in parking mode either when not in measurement mode or when not used/enabled at all for a given application. The circuitry is designed to maintain the sensing channels 102 in a linear region of operation, to optimize power consumption, to enable any combination of channels 102 in either parking or measurement modes and to provide a seamless transition between modes.

FIGS. 14-19 illustrates low power circuitry for biasing a multi-channel gas sensor array 305. The circuitry described consists of two main blocks. The first block where the sensors 102 are not being measured, is referred to as the "parking circuit". The other is used when the sensors 102 are being measured and is referred to as the "measurement circuit". The electrical characteristics of interest are both the static resistance and the differential resistance. A sensing element 102 in this case refers to the portion of a sensor 102, which has been functionalized by nanomaterials 208. The sensor channel is the sensing element 102, the substrate, and other hardware providing the connection between the sensing element 102 to the board.

Figure 14:
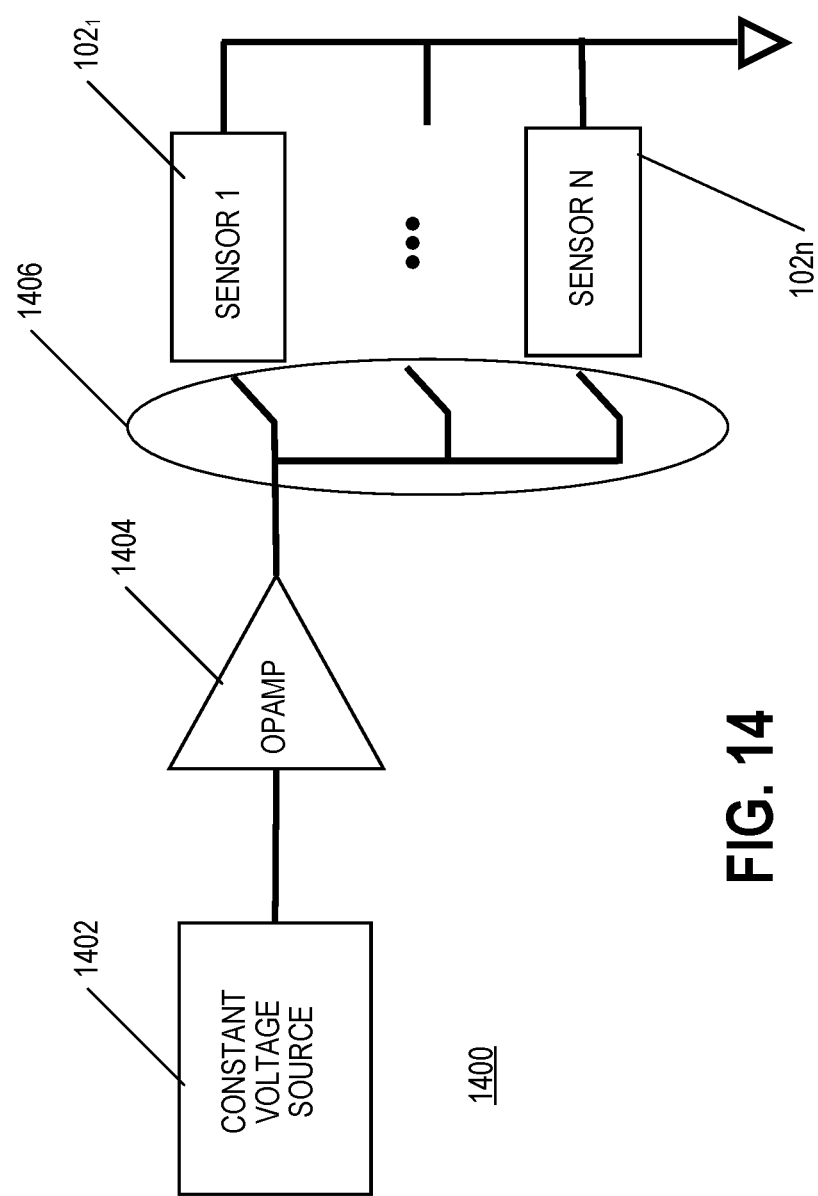
FIG. 14 is a diagram illustrating a parking circuit that can be included in the system of FIG. 4 in accordance with one example embodiment.

FIG. 14 is a diagram illustrating a parking circuit 1400 in accordance with one example embodiment. The parking circuit 1400 allows for the connection of N sensors 102 for conditioning while waiting to be measured. The parking circuit 1400 consists of a constant voltage source 1402, an OP AMP 1404 and Single Pole Single Throw switches (SPST) 1406 to connect/disconnect each sensor 102 independently.

The voltage reference 1402 can be a precision 1V reference conditioned using a buffer amplifier. The reference voltage can be anything below 2.5V. 1V is chosen for certain embodiments for maximum compatibility with the various sensing elements. This keeps the sensors 102 within the linear region, as well as reduces the overall power consumption. 1V also provides a reasonable range of measurement when used in conjunction with digital logic levels of microcontroller circuitry.

In addition, the electrical current to each sensor 102 can be limited to 1 mA to prevent damage to the sensing element 102. A simple series resistor can be used as a cost-effective means of limiting the current. This further protects the entire circuit or system from a short circuit.

The SPST switches 1406 provide a means to individually connect or disconnect sensors 102 to the voltage reference 1402. This allows the system to dynamically control a subset of active sensors 102, modulating the overall power consumption. If a sensor 102 falls below a certain resistance value, it can be disabled to maintain current consumption below an acceptable limit. Additionally, the same sensor chip 304 configuration can be used in multiple applications, and only have a subset of the sensor channels 102 selectively enabled. Furthermore, if a specific channel 102 is identified to be non-functional or "broken" it can be disconnected and ignored by the application.

Figure 4:
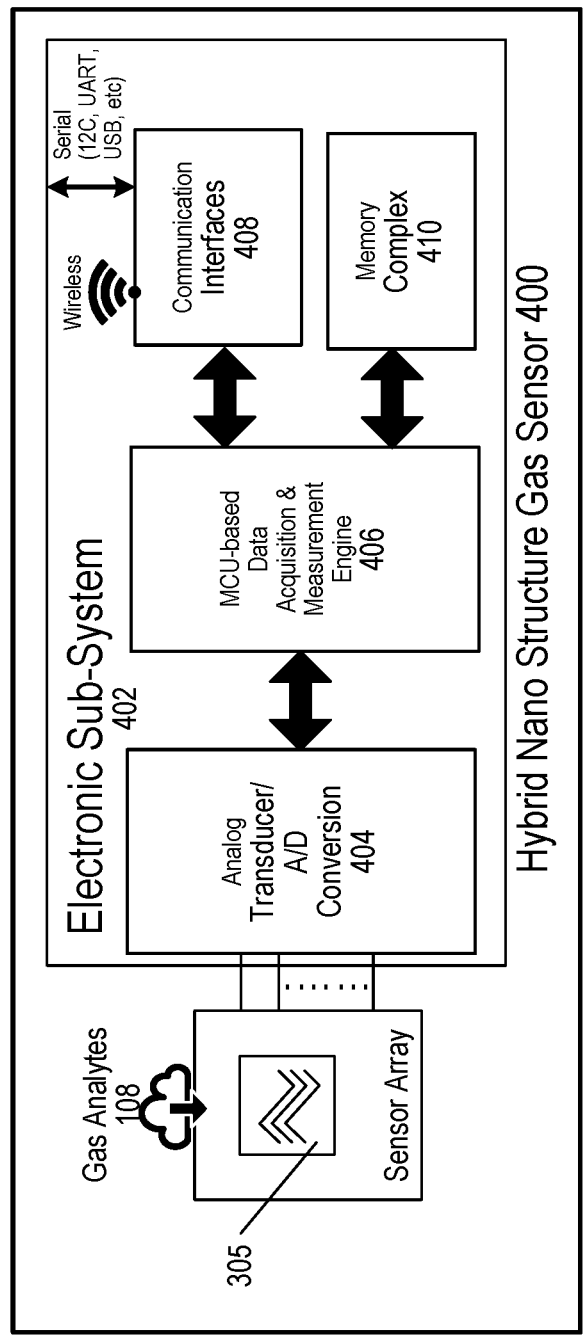
FIG. 4 is a block diagram of the hybrid nanostructure gas sensor system that incorporates the hybrid nanostructure gas sensing array of FIG. 3 in accordance with one embodiment.
Figure 15:
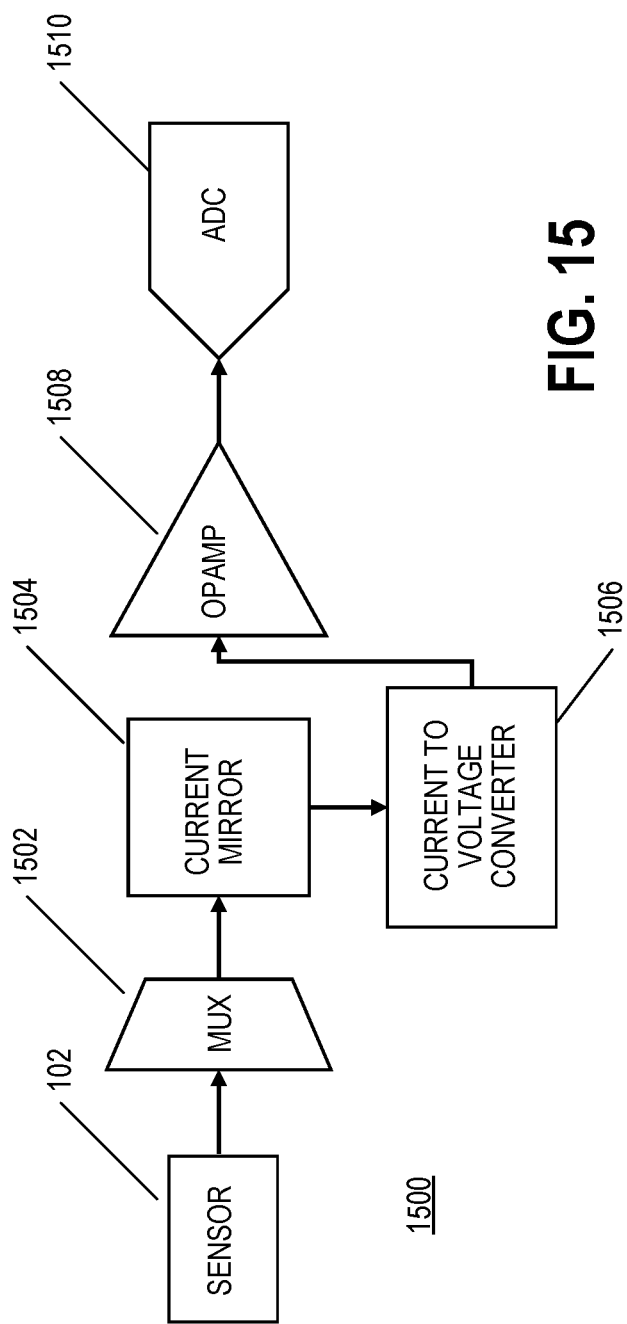
FIG. 15 is a diagram illustrating an example measurement circuit that can be included in the system of FIG. 4 in accordance with one embodiment.

FIG. 15 is a diagram illustrating an example measurement circuit 1500 that can be included in the system of FIG. 4 in accordance with one embodiment. The measurement circuit 1500, in this example, consists of a multiplexer 1502, current mirror 1504, a current to voltage stage 1506, and a gain stage 1508. The output of the measurement circuit can be sent to the ADC 1510 within element 404 of system 400. A separate measurement circuit which isolates a single or set of sensing elements 102 allows for minimizing cross-talk between the sensors 102. The sensors 102 of interest are connected to their own reference voltage when being measured, preventing transients on the parked sensors 102 from affecting the supplied voltage or noise.

Figure 16:
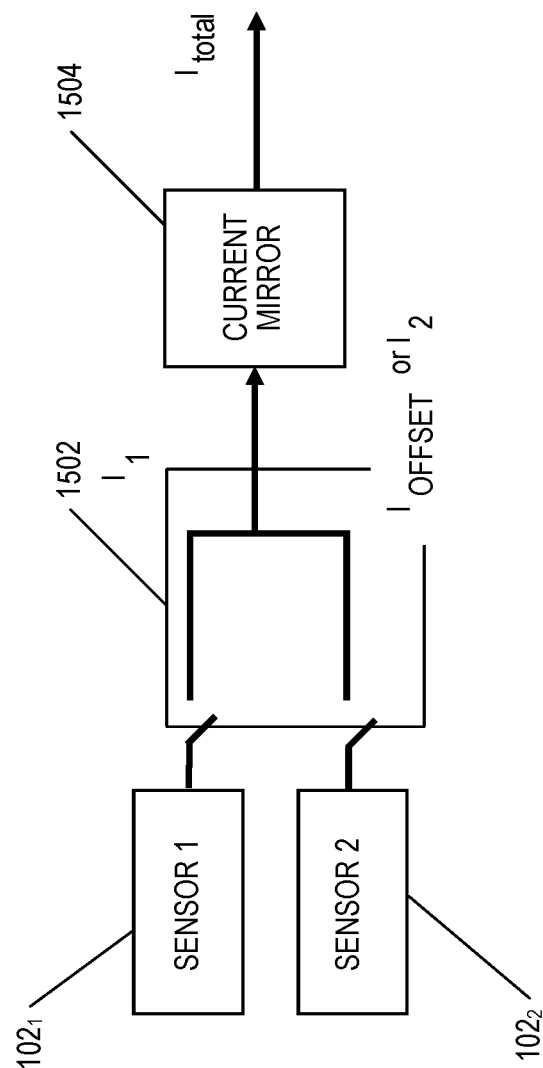
FIG. 16 is a diagram of an example multiplexer implementation that can be included in the circuit of FIG. 15 in accordance with one embodiment.

FIG. 16 is a diagram if an example multiplexer 1502 implementation in accordance with one embodiment. The multiplexer 1502 allows for selecting 1 of N channels 102. In certain embodiments, the multiplexer 1502 can be implemented as SPST switches. Combining multiple resistances in parallel can act as an offset current to the sensor channel(s) 102 of interest. For example, combining a 10 kOhm sensor with a 1 MOhm sensor yields a 0.101 mA current versus measuring the 1 MOhm sensor alone which would provide 0.001 mA.

Take two sensing elements 102, which are used for the same gas with one saturating at a lower concentration, causing the resistance to plateau. If sensor element '1' reaches a plateau at 100 ppb, and sensor element '2' only starts showing response at 100 ppb and plateaus at 1000 ppb, these can both be simultaneously connected and measured to cover the entirety of the range from 0 ppb to 1000 ppb. From 0-100 ppb, sensor '2' acts as an offset only while sensor '1' shows a change in resistance. From 100 ppb to 1000 ppb sensor '1' acts as an offset only whereas sensor '2' shows a change in resistance.

In the case of multiple channels 102, using an offset of 10 kOhm along with a 1 MOhm resistor can reduce the settling time if switching from a sensor channel 102 with resistance value closer to the smaller of the two. This allows the overall current to be on the same order of magnitude, reducing the settling time.

The circuit can also act as a current adder for multiple sensors 102, while at the same time cancelling out uncertainty and noise. If multiple sensors 102 of 1 MOhm are connected, instead of measuring the change of 0.001 mA it becomes a measurement of N*0.001 mA. White noise introduced by the system can also be cancelled out by averaging these signals providing a sqrt(N) factor of improvement. This can also act as a means of speeding up measurement time if there are multiple sensing elements 102 with similar properties.

Figure 17:
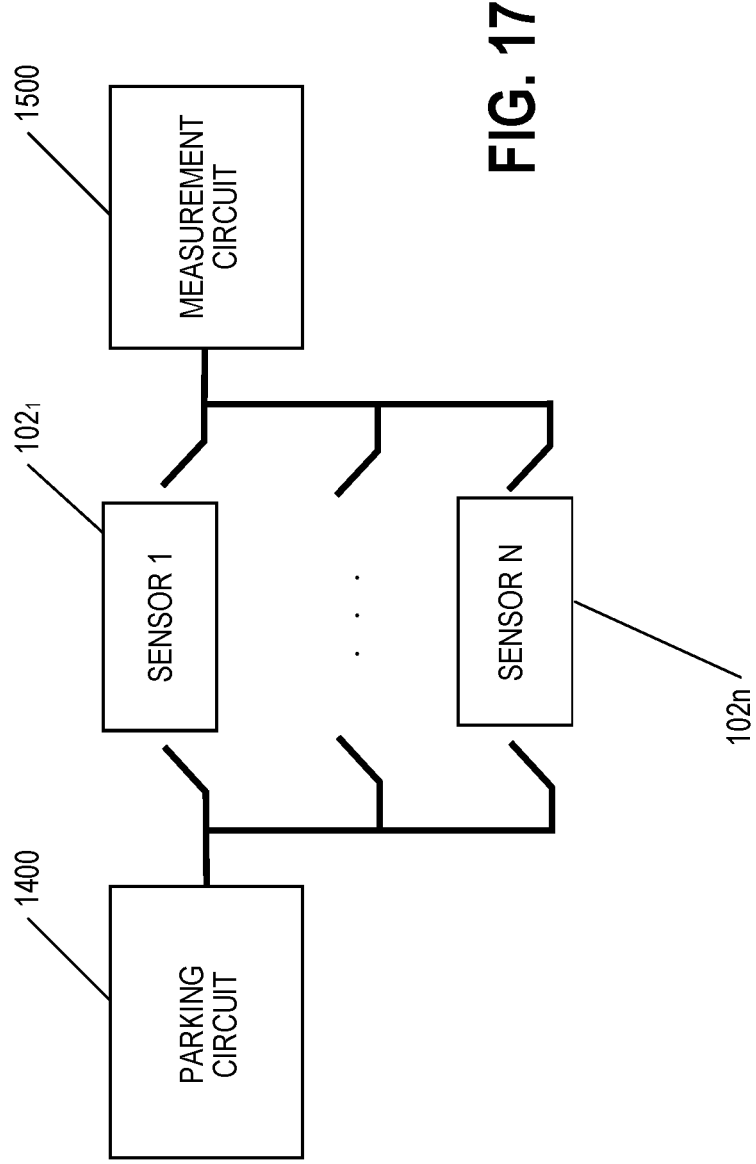
FIG. 17 is a diagram illustrating an example parking circuit and example measurement circuit coupled with a plurality of sensors.

FIG. 17 is a diagram illustrating an example parking circuit 1400 and example measurement circuit 1500 coupled with a plurality of sensors 102. The multiplexer circuit 1502 and the connection with the parking circuit 1400 allows for a make-before-break operation. A single channel 102 can be connected to both the measurement 1500 and parking circuit 1400 simultaneously. The sensor channel 102 is then disconnected from the parking circuit 1400 while connected to the measurement circuit 1500. As they are both at the same voltage or potential, this allows for minimizing the transient load on the sensor channel and the sensing element 102.

FIG. 18 is a diagram illustrating an OP-AMP circuit 1800 that can be used in place of the current mirror 1504 of FIG. 15. The current mirror is one method of creating a constant voltage source, but a similar circuit with an OP-AMP could be utilized. The gain stage is implemented as a separate programmable gain amplifier but can be integrated with the current mirror design if desired.

An example of integrated gain could be a current mirror that has different mirroring ratios, such as but not limited to 1:1, 1:2, 1:4, 1:8, and so on.

In this implementation of a current mirror, the voltage applied to the sensing element 102 is also 1V, but again has the same properties as the parking circuit 1400. It should be less than 2.5V and be current limited to prevent damage to the sensing element 102.

Figure 19:
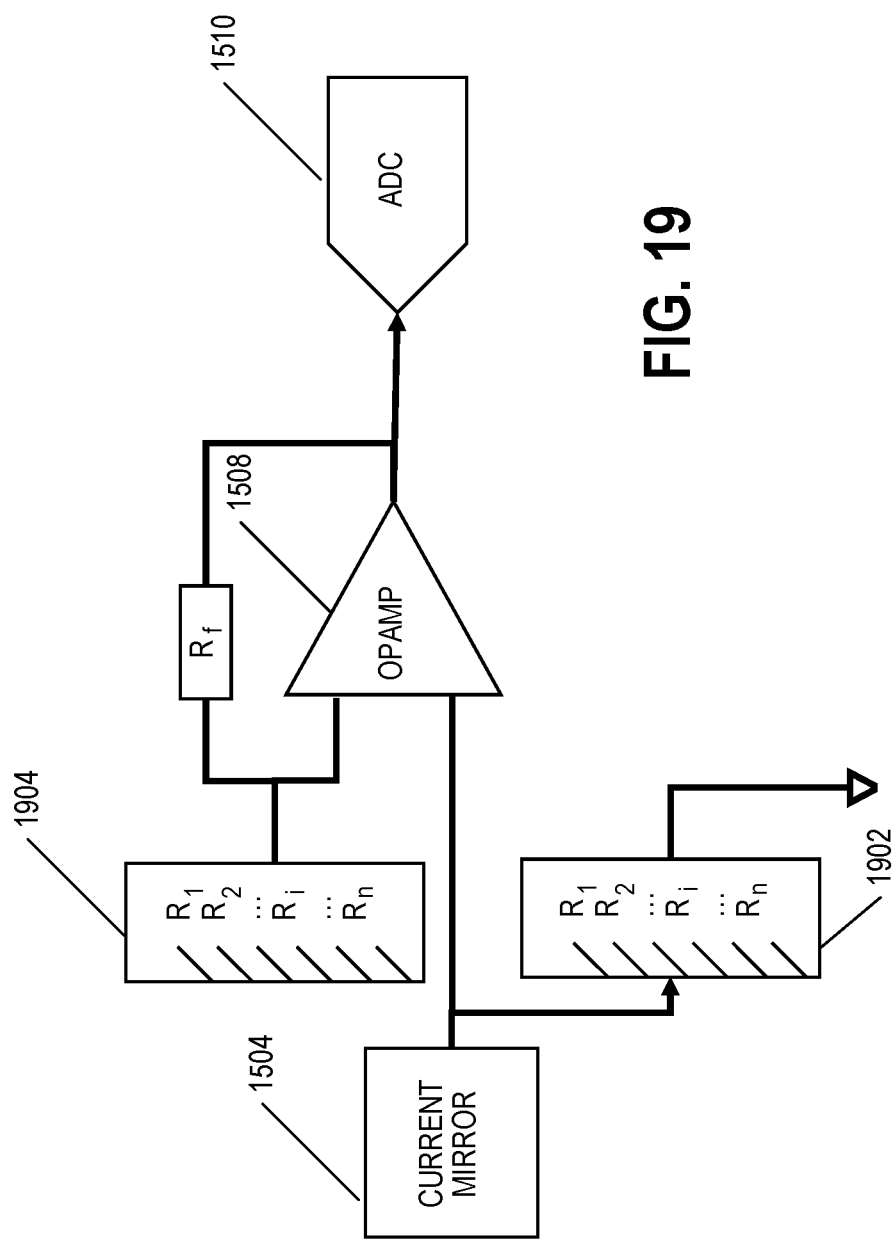
FIG. 19 is a diagram illustrating a circuit for converting the output of the current mirror of the measurement circuit of FIG. 15 into an analog signal that can be sent to the ADC included in the system of FIG. 4.

FIG. 19 is a diagram illustrating a circuit for converting the output of the current mirror 1504 into an analog signal that can be sent to the ADC 1510. The output of the current mirror 1504 is connected to a resistor Rn to convert the current into a voltage for measurement with an ADC 1510. There are 8 different resistors (Rn) in resistor network 1902, connected to SPST switches (not shown) on the output. Each resistor Rn of network 1902 can be connected in parallel to increase the number of possible matching resistors. A resistance that is the same value or larger than that of the sensors 102 is ideal, allowing for the output voltage to be at least 1V.

The output resistor Rn in network 1902 is chosen to maximize the voltage for measurement. Depending on the reference on the ADC 1510 and the known resistance range of the sensors 102 various resistance values can be made.

The current across the sensor (Is) is the same as the current into the mirror (Iin), which is calculated by the voltage across the sensors (Vs) divided by the resistance of the sensor (Rs): Iin=Is=Vs/Rs.

The current output is set by the current mirror gain ratio (G1): Iout=G1*Vs/Rs.

The voltage desired at the input of the ADC 1510 is dependent on the reference. The target threshold for the ADC 1510 is typically within 70% to 90% to maximize the signal while allowing additional headroom for the sensor to change. Thus:

$$Vadc*ADCthreshold=Rvs*Iout \text{ or } Rvs=[(Vadc*ADCthreshold)/(G1*Vs)]*Rs.$$

For example, the sensor 102 has a voltage of 1V, the ADC 1510 has a 2.5V reference, and the current mirror 1504 provides a 1:1 ratio, then:

$$Rvs@70\%=1.75*Rs \text{ and } Rvs@90\%=2.25*Rs.$$

In this example, there are 8 geometrically spaced resistors (Rn) in network 1902 ranging from 17.8 kOhms to 5 MOhms but values can be spaced asymmetrically if the sensing elements 102 are not evenly spaced in terms of resistance values. This entire resistor block can be replaced with a transimpedance amplifier (TIA) as an alternative means of converting current to voltage.

Additionally, there is a secondary gain stage which consists of an OP-AMP 1508 with 8 resistors (Rn) in network 1904 connected to SPST switches (not shown). The same idea as with the initial voltage select resistor, can be applied here for the gain. In some implementations it may be ideal to have asymmetric spacing on the current to voltage conversion, and symmetric spacing on the secondary gain. One is specific to the resistance ranges of the sensing elements 102, and one is generic for the overall gain. This breaks the overall gain component, G into two components of G1 and G2:

$$Rvs=[(Vadc*ADCthreshold)/(G1*G2*Vs)]*Rs$$

The purpose of gain here is to provide the maximum input into the ADC 1510. In this case a 2.5V reference is used and the circuit attempts to provide as close as possible to 2.5V, while still maintaining enough room for changes in the sensing element's resistance to avoid saturating the signal. A SAR ADC 1510 can be used to allow for oversampling and reducing noise, and error stack up in the preceding circuit stages.

Potential sources of error stack up that are introduced in each sample, include but are not limited to the voltage reference error, current mirror transfer from input to output, OP-AMP 1508 noise gain, thermal coupling, etc.

Figure 5:
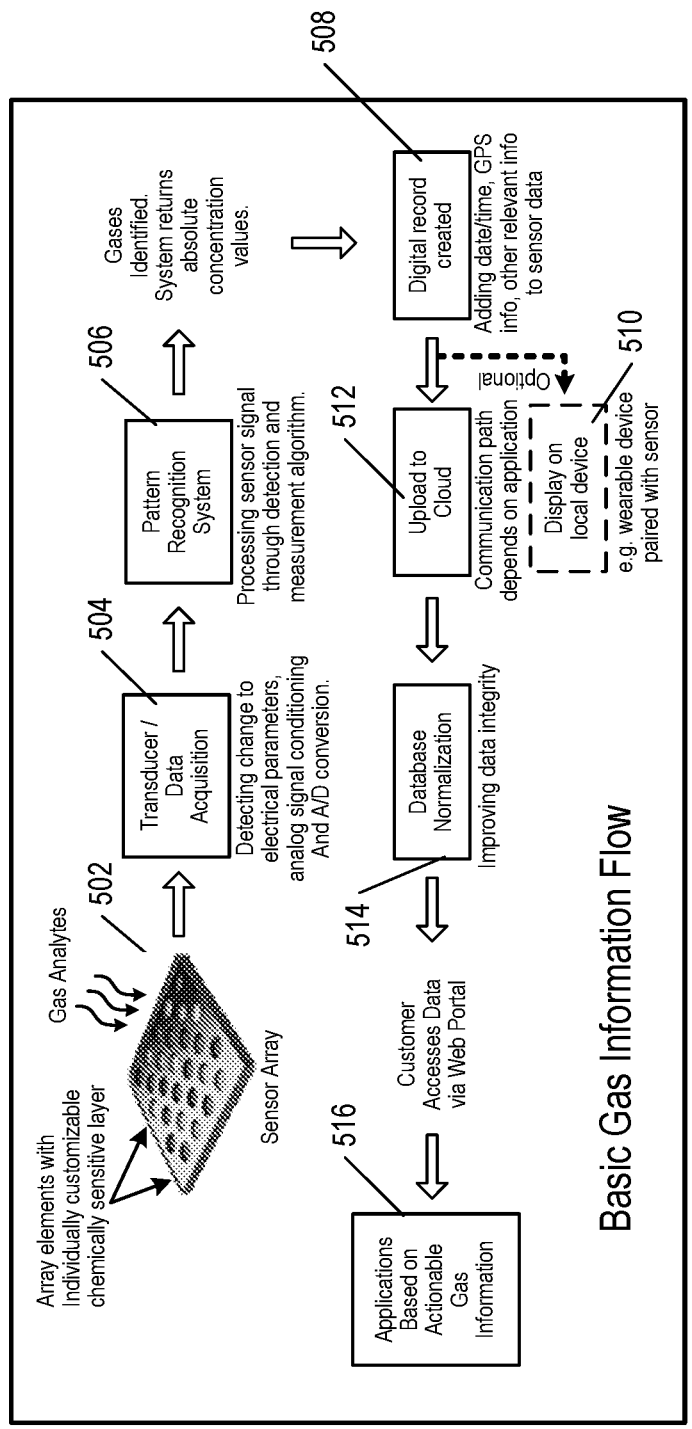
FIG. 5 is a chart showing the flow of gas information through the hybrid nanostructure gas sensor system of FIG. 4.

FIG. 5 shows the basic flow of information through a complete nano gas sensor system, such as system 400 described in more detail below. When the sensor array 305 is exposed to the mixture of gas analytes 108 in its environment, in step 502, the sensitive layers 104 of the materials deposited on the sensor elements 102, or sensing channels react, according to their formulation 202, to the presence of specific component gases in the mixture. The reaction causes a change in the electrical characteristics of the sensing channels 102, which is captured by the transducer in the electronics sub-system, in step 504, and then analyzed by the pattern recognition system programmed in the sub-system MCU, in step 506. The output is an absolute value of the concentration of the gases being detected. This is then combined, in step 508, with other desirable meta-data such as time or geo-location into a digital record. This digital record (or a portion of it) can optionally be displayed locally in step 510 (for example, in the case of a wearable application where the sensor is paired to a phone, the data can be further manipulated and displayed by a specially written mobile application running on the phone). More importantly the data is uploaded, via a mechanism that is dependent on the application, to a Cloud data platform in step 512, where the data can be normalized in step 514 and accessed via various application in step 516.

The fourth element is a MCU-based data acquisition and measurement engine, or digital backend, which also provides additional functions such as overall sensor system management and communication, as necessary with encryption, to and from a larger system into which the sensor is embedded. The digital back end consists of a microcontroller, integrated circuits, and data acquisition optimization algorithms. The digital back-end acts as the controller for the analog front-end. The biasing and the gain settings for each channel are optimized by the digital back end. This includes, but is not limited to power consumption, sampling time, sampling period, and signal-to-noise ratio.

Figure 20:
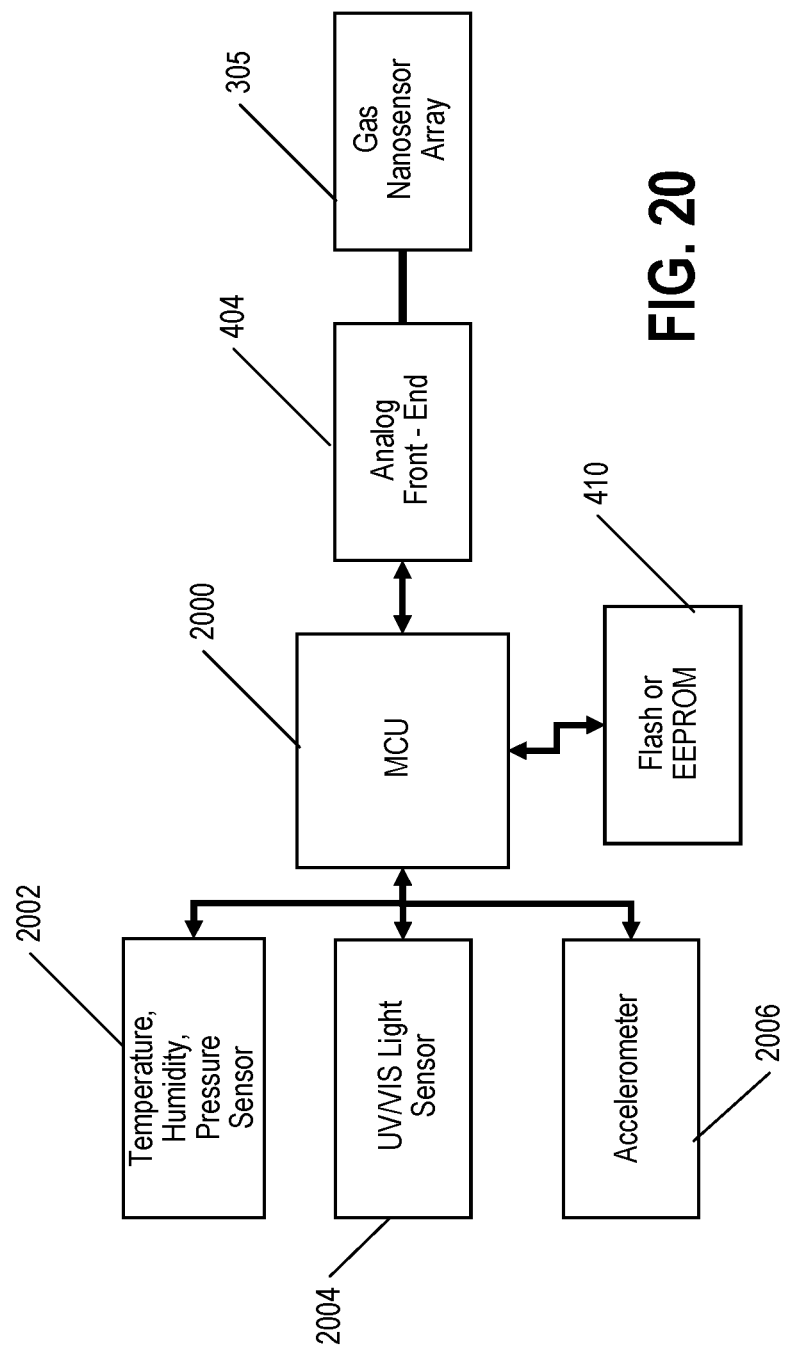
FIG. 20 is a diagram illustrating certain components of the digital backend of the system of FIG. 4 in accordance with one embodiment.

FIG. 20 is a diagram illustrating certain components of the digital backend 406 in accordance with one embodiment. In certain embodiments of the system 400, an additional temperature and humidity sensor 2002 can be added, as well as other sensors such as a barometer, UV and visible light sensor 2004, etc. These are connected through digital interfaces such as I2C, SPI, UART, etc., to MCU 2000. The sensor data from array 305 is used as one of the inputs to a pattern recognition algorithm as described herein.

The analog front end 404 provides a range of gain settings to be controlled and stored by the digital back end 406. The initial calibration step attempts to maximize the fill of the ADC 1510 between 70% to 90% of the analog reference. The fill values can be changed depending on the integral non-linearity (INL) or differential non-linearity (DNL) of the ADC 1510. This can be either an iterative search, increasing the gain in a linear fashion, a binary search through the range of gain settings, or a direct calculation. Each sensor channel 102 goes through this process and the selected gain settings are stored in memory. After each measurement, the gain settings are updated for the next cycle.

The measurement of the external sensors 2002-2006 are synchronized with that of the nano gas sensors 102 to minimize the phase delay. For example, if a humidity sensor takes 25 ms to make a conversion and provide a result, the conversion will be started 25 ms before the nano gas sensors' measurement will be completed.

Figure 21:
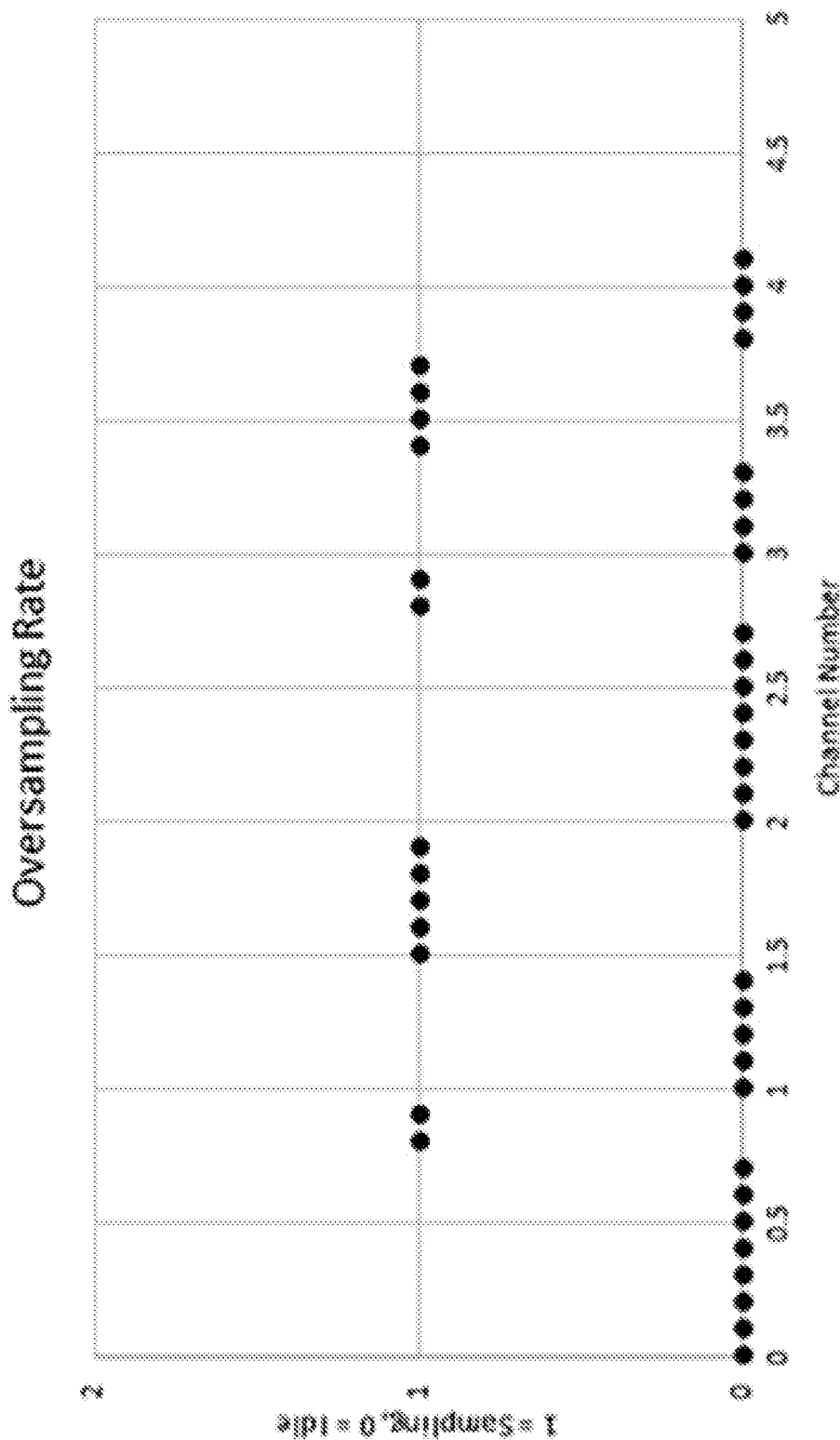
FIG. 21 is a graph illustrating and an example plot of dynamic oversampling rate that can be implemented in the digital backend system of FIG. 4 in accordance with one embodiment.

As illustrated in FIG. 21, oversampling of the data can be obtained by taking repeated ADC readings and averaging. This oversampling rate is adjusted to minimize the latency between each channel 102. Depending on the resistance range of the sensor channel 102, the oversampling factor can be increased.

Figure 22:
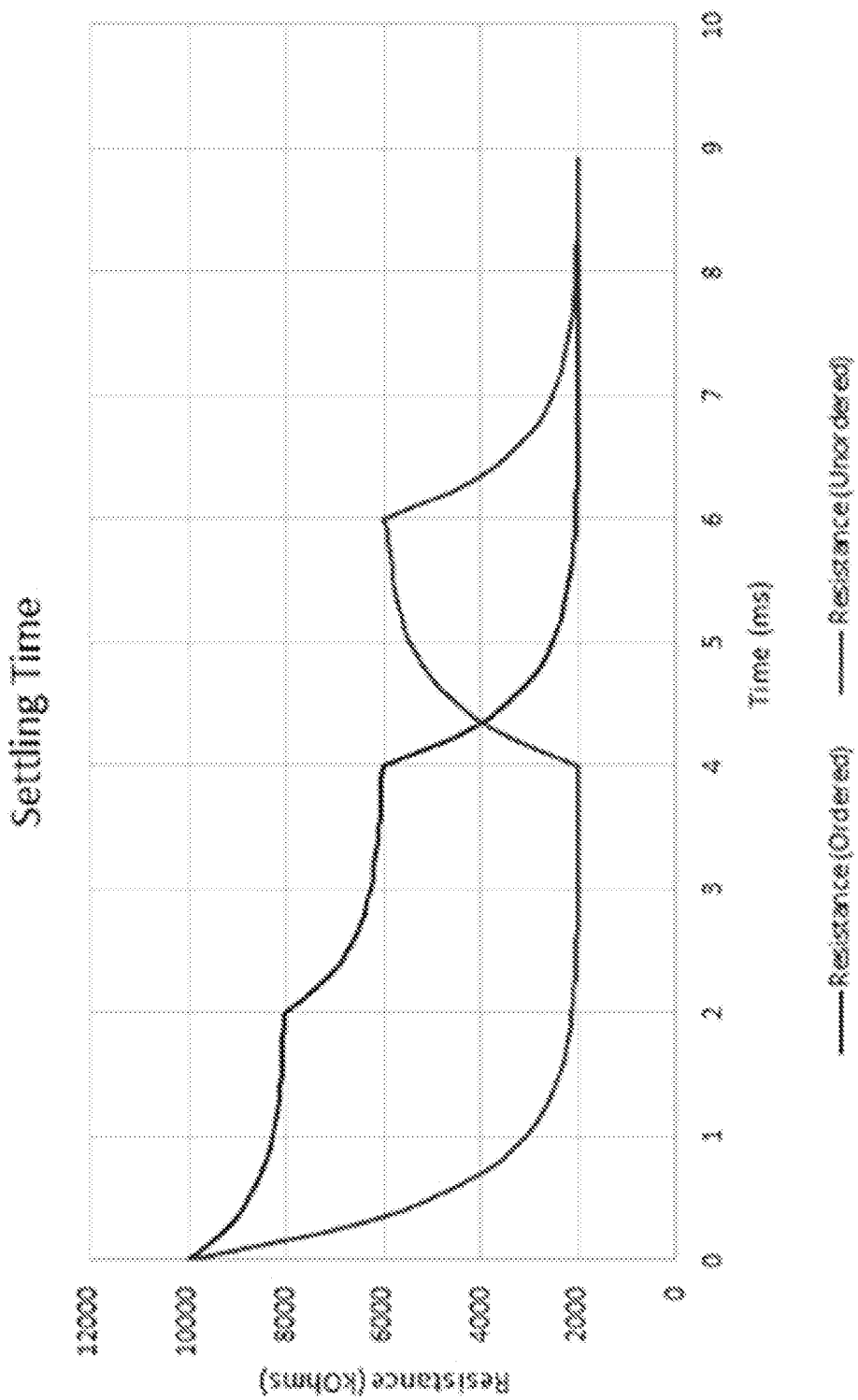
FIG. 22 is a graph illustrating and an example plot of optimized vs non-optimized settling time that can be implemented in the digital backend system of FIG. 4 in accordance with one embodiment.

The order the channels 102 are sampled can be optimized to reduce the data acquisition time. Sensors 102 can be measured in either ascending or descending order, by voltage or resistance. This minimizes the delta between successive channels, thereby reducing the settling time required between each channel as illustrated in the graph of FIG. 22.

The digital system also disables sensor channels 102 that are not of interest. This includes channels 102 that are determined to be outliers, damaged or otherwise non-responsive. Outliers are determined based on the expected resistance range of sensor channels 102. Additionally, if a sensor chip 304 contains multiple channels 102 of the same material, deviations from the average response curve can be used to identify outliers.

Damaged sensors 102 may be either a short or an open circuit. In either case the resistance is either too low or too high and can be disconnected from the circuit and ignored when iterating through the channels 102. The cutoff threshold for large resistances depends on the lower detection limit (LDL) of the application, the sensitivity of the sensing element 102, and the effective resolution of the ADC 1510. If the sensitivity of a sensing element 102 is known to be a certain percentage per ppb of gas, the threshold can be calculated with the following, where SnR is the desired signal-to-noise ratio.

$$[V\text{bias}/(LDL*R\text{sensitivity})]*Gain > SnR*[(AD\text{Cresolution})/V\text{aref}]$$

Figure 23:
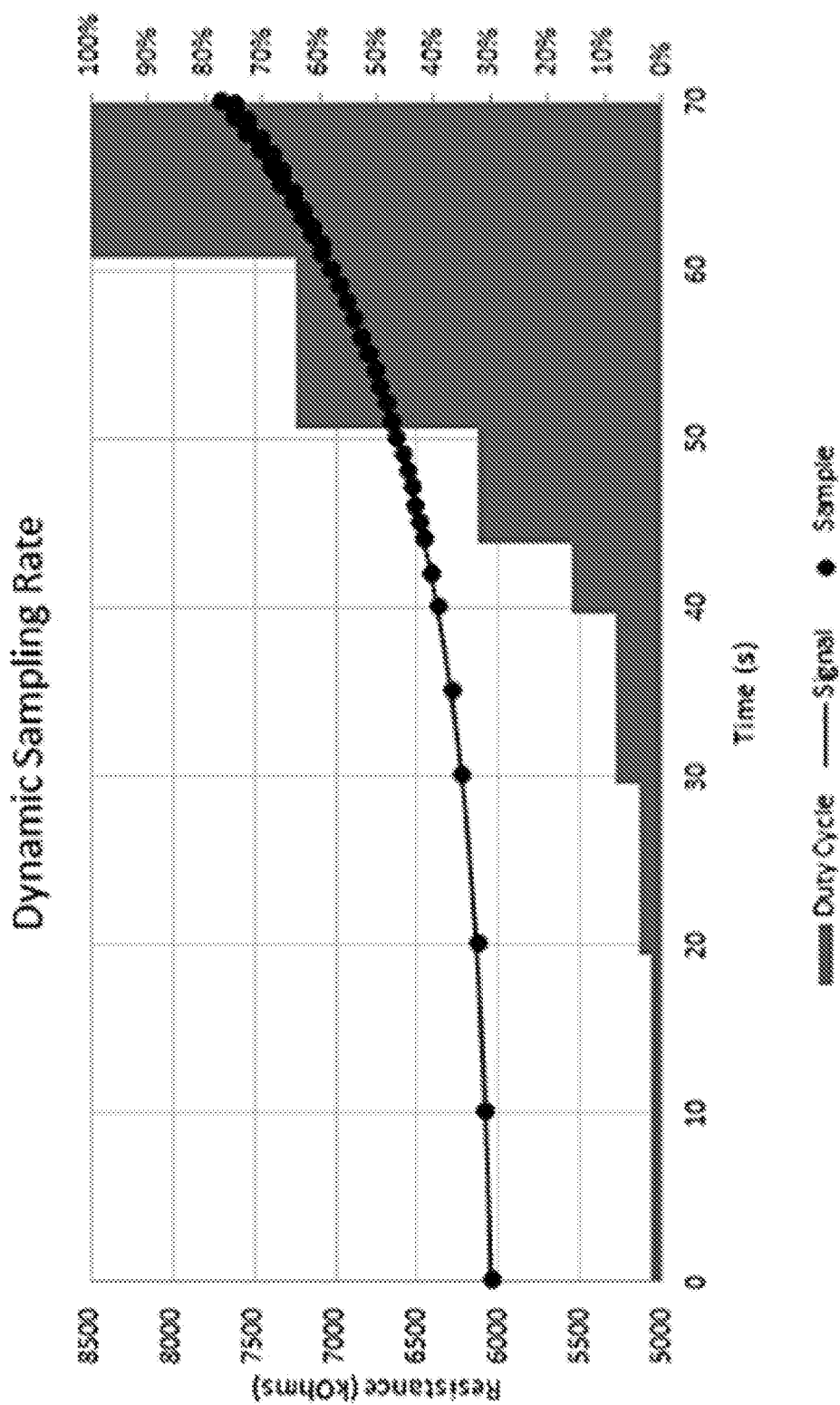
FIG. 23 is a graph illustrating and an example plot of dynamic sampling rate over signal, and duty cycle that can be implemented in the digital backend system of FIG. 4 in accordance with one embodiment.

As illustrated in FIG. 23 the sampling rate can be dynamically modulated depending on the detection time and application. Dynamic modulation allows for reducing the duty cycle of the digital back-end 406, reducing overall power consumption. In situations where the gas concentration is not expected to rapidly change, sampling rate can be reduced. Additionally, depending on the desired response time of the sensor the sampling rate may be decreased or increased.

For any given application, the sampling rate does not have to be constant. It can be increased as a change in the sensors electrical properties are being detected. For example, there can be a detection period where the sampling rate is relatively slow, at 1 sample per second. As the resistance changes exceeds a given threshold, this can be increased to 5 samples per second.

The third and fourth elements are designed to work together and to form a complete electronic sub-system specifically tuned to work with the array of sensing channels 305 implemented as a separate component. The transducer 404 is firmware configurable to provide optimal A/D conversion for a pattern recognition system running on the MCU 406 and implementing the gas detection and measurement algorithm(s).

The electronic sub-system 402 is suitable for implementation in a variety of technologies depending on target use model and technical/cost trade-offs. PCB implementations will enable quick turn-around and the declination of a family of related products (for instance with different communication interfaces) to support multiple form factors and applications with the same core electronics. When size and power/performance trade-offs are critical, the electronic sub-system 402 is implemented as a System On a Chip (SoC), which can then be integrated together with a MEMS chip carrying the array of sensing channels 305 into a System In a Package (SIP).

The sensor die 304 must then be assembled with the sensor's electronic sub-system to complete the hybrid nanostructure gas sensor 400 for which a functional block diagram is shown in FIG. 4.

The electronic sub-system can be implemented as a PCB or as a SoC. If the PCB route is followed the sensor die 304 can be either wire-bonded to the electronic sub-system 402 board after completion of the PCB Assembly (PCBA) step or, if the sensor die 304 has itself been individually assembled in a SMT package, it can be soldered on the board as part of PCBA. If the SoC route is followed, the sensor die together with the SoC die of the electronic sub-system 402 can be stacked and assembled together into a single package (System In a Package) or each can possibly be assembled into individual packages.

Either assembled into its own package or assembled into a SIP, the sensor chip 304 must be exposed to ambient air. Therefore, the package lid must include a hole of sufficient size over the sensor.

Testing happens at various points of the sensor manufacturing process.

After sensor functionalization (deposition of the molecular formulations 204), certain handling precautions must be followed for the rest of the product manufacturing flow to prevent accidental damage to the sensor chip 304 (e.g. a pick and place tool must not make contact with the surface of the sensing elements).

The fifth element is the gas detection and measurement algorithm. The algorithm implements a method for predicting target gas concentration by reading the hybrid nanostructure sensor array's multivariate output and processing it inside the algorithm. The algorithm analyzes sensor signals in real time and outputs estimated values for concentrations of target gases. The algorithm development is based on models that are specific to the materials deposited on the sensing channels of the sensor array. These models are trained based on the collection of an abundant volume of data in the laboratory (multiple concentrations of target gases, combinations of gases, various values of temperature, relative humidity and other environmental parameters). Sophisticated supervised modeling techniques are used to attain the best possible agreement between true and predicted values of target gas concentrations. Prior to deployment, extensive lab and field testing is carried out to optimize model performance and finalize sensor validation.

The first five elements together constitute the hybrid nanostructure gas sensor 400 and provide all the functionality necessary to detect multiple gases 108 in ambient air at the same time and to report their absolute concentrations. The sensing capability of the hybrid nanostructure sensor array 305 is always "on" and the gas detection and measurement algorithm makes it possible for the sensor 400 to require no special calibration step before use and to remain self-calibrating through its operational life.

The sixth element is the Cloud Data Platform that enables a virtually unlimited number of sensors 400 deployed as part of a virtually unlimited number of applications to be hosted in a global database where big data techniques can be used to analyze, query and visualize the information to infer actionable insight. The use of a Cloud-based environment provides all the necessary flexibility to customize how the data can be partitioned, organized, protected and accessed based on the rights of individual tenants.

The Cloud data platform provides another layer of sophistication to the system by allowing Cloud applications to operate on the data set. For instance, sensors 400 that are located in the same vicinity would typically report consistent gas values thus allowing errant results to be identified and a possible malfunction of one node of a network of sensors investigated.

The continuous collection of highly granular gas information by a multitude of connected devices (IoT—Internet Of Things) is critical to go beyond monitoring to generate actionable insight from large amount of collected data (Big Data Analytics, Artificial Intelligence).

A few application examples are highlighted below.

Example 1

We take 20,000 breaths every day and the air we breathe impacts our health —the science is already clear on this— but we rarely know what is in the air we breathe. To take meaningful action, consumers, scientists, public officials and business owners need the ability to measure air pollution at a personal, local and granular level which has, before this invention, been impossible due to the limitations of commercially available gas sensors mentioned above.

Mounting evidence suggests that prenatal and early life exposure to common environmental toxins, such as air pollution from fossil fuels, can cause lasting damage to the developing human brain. These effects are especially pronounced in highly vulnerable fetuses, babies, and toddlers as most of the brain's structural and functional architecture is established during these early developmental periods. These disruptions to healthy brain development can cause various cognitive, emotional, and behavioral problems in later infancy and childhood.

The sensor technology described herein allows researchers to gather highly detailed, accurate data about pregnant women's exposure to environmental air pollution and the resulting effects on the developing brain. The availability of this technology will represent a profound advance on current methods and efforts in the field that will have far-reaching consequences for improving newborn and child health throughout the world.

More generally, personal air monitoring and local indoor and outdoor monitoring will be a breakthrough for scientific research, healthcare interventions, personal preventive actions, advocacy and more.

The sensor technology described herein can deliver complete processing and gas results to a broad spectrum of smart systems under development for the Smart Cities of tomorrow. The sensor is designed for Plug and Play integration into IoT devices and the small form factor is compatible with a multitude of devices from LED lights to smart meters, to standalone monitoring stations, to non-stationary devices (drones, public vehicles, wearables, phones, etc.).

Example 2

The sensor technology described herein can be used in smart appliances such as connected refrigerators, that will help customers monitor food freshness, detect spoilage and the presence of harmful pesticide residues. The simultaneous, multi-gas, sensing capability of the invention will enable sensors that can recognize the gas patterns associated with the condition of specific foods.

Example 3

A network or grid of the sensors 400 described herein, can be integrated into industrial areas such as petrochemical complexes and oil refineries to allow companies to monitor the sites during regular operation (e.g. for leaks) or in the event of natural or human-made disasters. The sensors can also be installed in drones for data collection in hard to reach or potentially dangerous area. The ability of the technology to be deployed in wearables and in fixed and mobile networks will provide both personal protection and granular data across large area, allow the constant monitoring of a facility for preventive measures to be taken in a timely fashion, save critical time when urgent decision making is required and provide invaluable information to protect workers and emergency personnel.

The same technology can place powerful new tools in the hands of first responders and officials responsible for public safety and homeland security.

Figure 6:
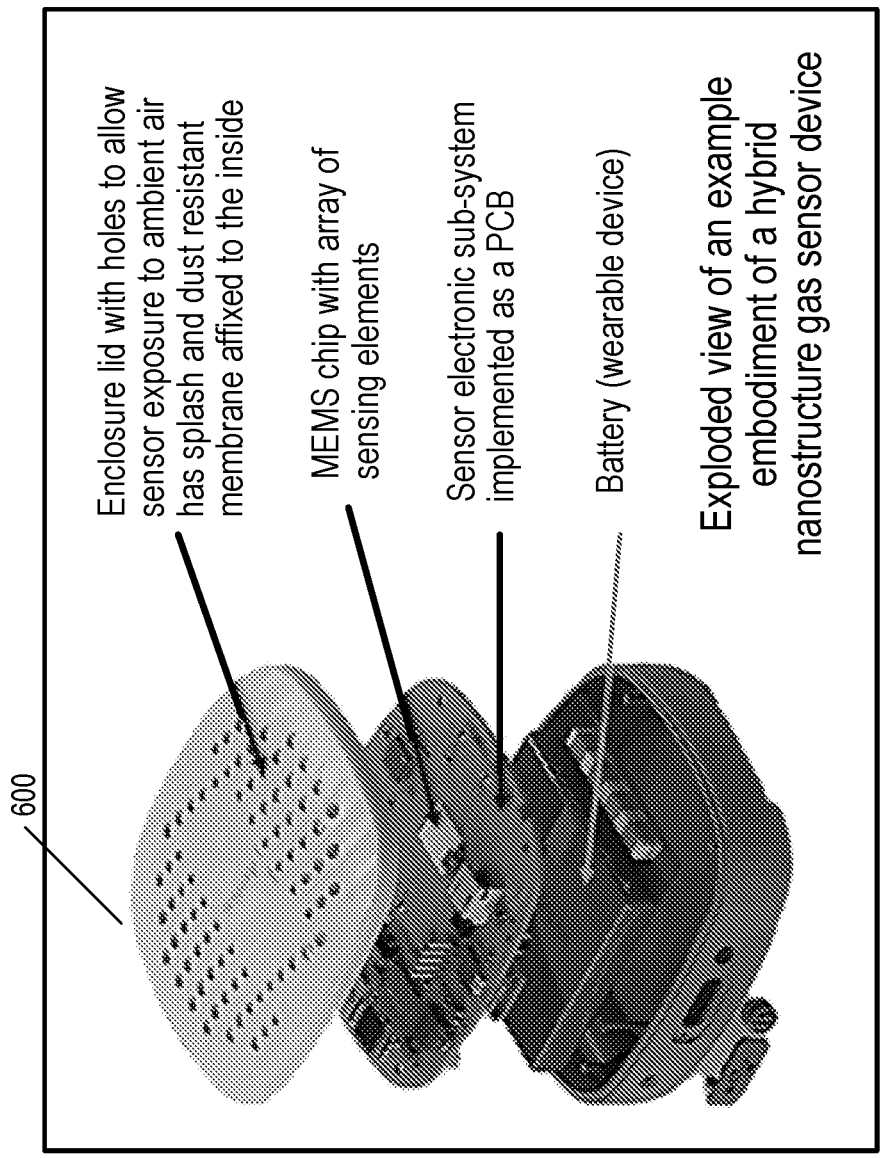
FIG. 6 is an exploded view of an example wearable product built around a PCB embodiment of the hybrid nanostructure gas sensor system of FIG. 4.

FIG. 6 shows an example product 600, in this case a battery-powered wearable device, with the sensor 400 implemented as a small PCB. The sensor technology lends itself to integration into any number of IoT devices. While the sensor does not need the active creation of an airflow to function, the sensitive layers 104 at the surface of the sensor must be exposed to ambient air and at the same time provided a reasonable amount of protection from dust and fluids. This is usually achieved by designing an air interface that ensures that the sensor 400 is behind a perforated shield (e.g. the lid of an enclosure) with a thin membrane (PTFE, 0.5 um mesh) being used to provide splash and dust protection. Outdoor applications may require the design of a more complicated air interface to meet the weather-proofing requirements.

Figure 7:
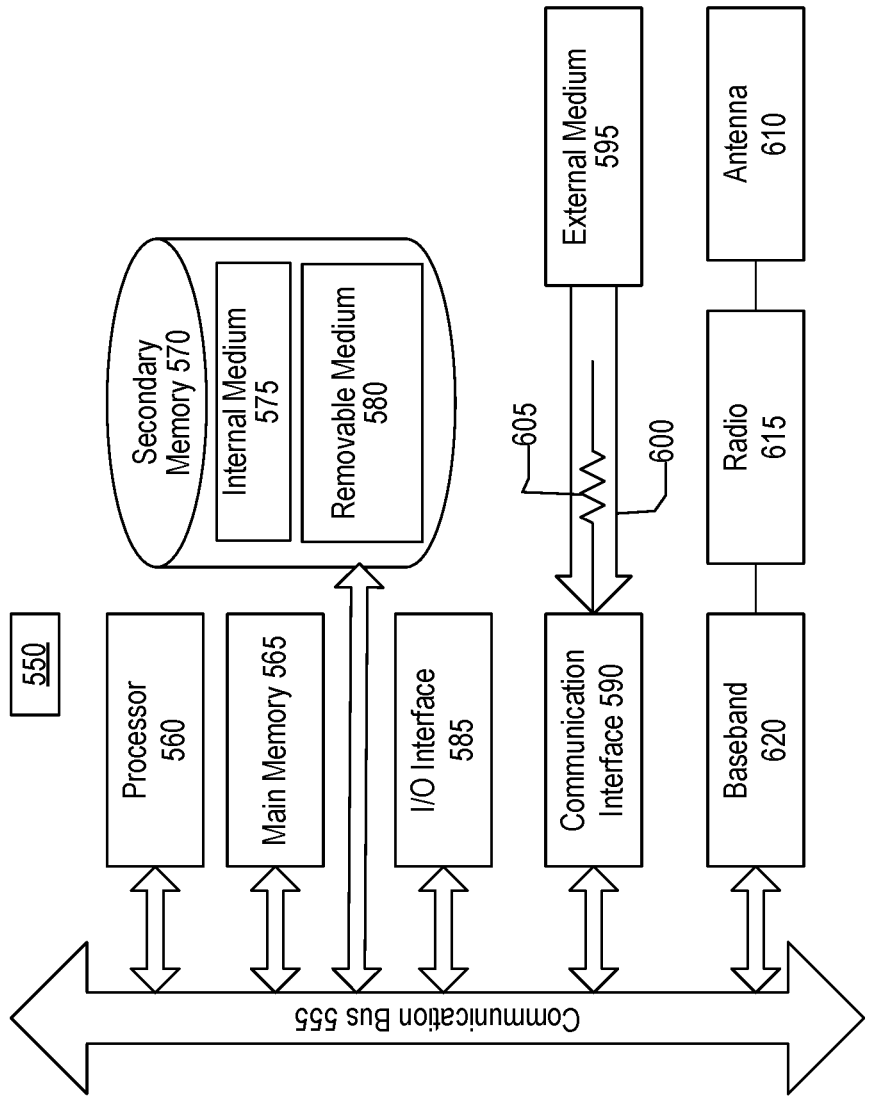
FIG. 7 is a block diagram illustrating an example wired or wireless system that can be used in connection with various embodiments described herein.

FIG. 7 is a block diagram illustrating an example wired or wireless system 550 that can be used in connection with various embodiments described herein. For example the system 550 can be used as or in conjunction with one or more of the platforms, devices or processes described above, and may represent components of a device, such as sensor 400, the corresponding backend or cloud server(s), and/or other devices described herein. The system 550 can be a server or any conventional personal computer, or any other processor-enabled device that is capable of wired or wireless data communication. Other computer systems and/or architectures may be also used, as will be clear to those skilled in the art.

The system 550 preferably includes one or more processors, such as processor 560. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 560. Examples of processors which may be used with system 550 include, without limitation, the Pentium® processor, Core i7® processor, and Xeon® processor, all of which are available from Intel Corporation of Santa Clara, Calif. Example processor that can be used in system 400 include the ARM family of processors and the new open source RISC V processor architecture.

The processor 560 is preferably connected to a communication bus 555. The communication bus 555 may include a data channel for facilitating information transfer between storage and other peripheral components of the system 550. The communication bus 555 further may provide a set of signals used for communication with the processor 560, including a data bus, address bus, and control bus (not shown). The communication bus 555 may comprise any standard or non-standard bus architecture such as, for example, bus architectures compliant with industry standard architecture (ISA), extended industry standard architecture (EISA), Micro Channel Architecture (MCA), peripheral component interconnect (PCI) local bus, or standards promulgated by the Institute of Electrical and Electronics Engineers (IEEE) including IEEE 488 general-purpose interface bus (GPIB), IEEE 696/S-100, and the like.

System 550 preferably includes a main memory 565 and may also include a secondary memory 570. The main memory 565 provides storage of instructions and data for programs executing on the processor 560, such as one or more of the functions and/or modules discussed above. It should be understood that programs stored in the memory and executed by processor 560 may be written and/or compiled according to any suitable language, including without limitation C/C++, Java, JavaScript, Pearl, Visual Basic, .NET, and the like. The main memory 565 is typically semiconductor-based memory such as dynamic random access memory (DRAM) and/or static random access memory (SRAM). Other semiconductor-based memory types include, for example, synchronous dynamic random access memory (SDRAM), Rambus dynamic random access memory (RDRAM), ferroelectric random access memory (FRAM), and the like, including read only memory (ROM).

The secondary memory 570 may optionally include an internal memory 575 and/or a removable medium 580, for example a floppy disk drive, a magnetic tape drive, a compact disc (CD) drive, a digital versatile disc (DVD) drive, other optical drive, a flash memory drive, etc. The removable medium 580 is read from and/or written to in a well-known manner. Removable storage medium 580 may be, for example, a floppy disk, magnetic tape, CD, DVD, SD card, etc.

The removable storage medium 580 is a non-transitory computer-readable medium having stored thereon computer executable code (i.e., software) and/or data. The computer software or data stored on the removable storage medium 580 is read into the system 550 for execution by the processor 560.

In alternative embodiments, secondary memory 570 may include other similar means for allowing computer programs or other data or instructions to be loaded into the system 550. Such means may include, for example, an external storage medium 595 and an interface 590. Examples of external storage medium 595 may include an external hard disk drive or an external optical drive, or and external magneto-optical drive.

Other examples of secondary memory 570 may include semiconductor-based memory such as programmable read-only memory (PROM), erasable programmable read-only memory (EPROM), electrically erasable read-only memory (EEPROM), or flash memory (block oriented memory similar to EEPROM). Also included are any other removable storage media 580 and communication interface 590, which allow software and data to be transferred from an external medium 595 to the system 550.

System 550 may include a communication interface 590. The communication interface 590 allows software and data to be transferred between system 550 and external devices (e.g. printers), networks, or information sources. For example, computer software or executable code may be transferred to system 550 from a network server via communication interface 590. Examples of communication interface 590 include a built-in network adapter, network interface card (NIC), Personal Computer Memory Card International Association (PCMCIA) network card, card bus network adapter, wireless network adapter, Universal Serial Bus (USB) network adapter, modem, a network interface card (NIC), a wireless data card, a communications port, an infrared interface, an IEEE 1394 fire-wire, or any other device capable of interfacing system 550 with a network or another computing device.

Communication interface 590 preferably implements industry promulgated protocol standards, such as Ethernet IEEE 802 standards, Fiber Channel, digital subscriber line (DSL), asynchronous digital subscriber line (ADSL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on, but may also implement customized or non-standard interface protocols as well.

Software and data transferred via communication interface 590 are generally in the form of electrical communication signals 605. These signals 605 are preferably provided to communication interface 590 via a communication channel 600. In one embodiment, the communication channel 600 may be a wired or wireless network, or any variety of other communication links. Communication channel 600 carries signals 605 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software) is stored in the main memory 565 and/or the secondary memory 570. Computer programs can also be received via communication interface 590 and stored in the main memory 565 and/or the secondary memory 570. Such computer programs, when executed, enable the system 550 to perform the various functions of the present invention as previously described.

In this description, the term "computer readable medium" is used to refer to any non-transitory computer readable storage media used to provide computer executable code (e.g., software and computer programs) to the system 550. Examples of these media include main memory 565, secondary memory 570 (including internal memory 575, removable medium 580, and external storage medium 595), and any peripheral device communicatively coupled with communication interface 590 (including a network information server or other network device). These non-transitory computer readable mediums are means for providing executable code, programming instructions, and software to the system 550.

In an embodiment that is implemented using software, the software may be stored on a computer readable medium and loaded into the system 550 by way of removable medium 580, I/O interface 585, or communication interface 590. In such an embodiment, the software is loaded into the system 550 in the form of electrical communication signals 605. The software, when executed by the processor 560, preferably causes the processor 560 to perform the inventive features and functions previously described herein.

In an embodiment, I/O interface 585 provides an interface between one or more components of system 550 and one or more input and/or output devices. Example input devices include, without limitation, keyboards, touch screens or other touch-sensitive devices, biometric sensing devices, computer mice, trackballs, pen-based pointing devices, and the like. Examples of output devices include, without limitation, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), and the like.

The system 550 also includes optional wireless communication components that facilitate wireless communication over a voice and over a data network. The wireless communication components comprise an antenna system 610, a radio system 615 and a baseband system 620. In the system 550, radio frequency (RF) signals are transmitted and received over the air by the antenna system 610 under the management of the radio system 615.

In one embodiment, the antenna system 610 may comprise one or more antennae and one or more multiplexors (not shown) that perform a switching function to provide the antenna system 610 with transmit and receive signal paths. In the receive path, received RF signals can be coupled from a multiplexor to a low noise amplifier (not shown) that amplifies the received RF signal and sends the amplified signal to the radio system 615.

In alternative embodiments, the radio system 615 may comprise one or more radios that are configured to communicate over various frequencies. In one embodiment, the radio system 615 may combine a demodulator (not shown) and modulator (not shown) in one integrated circuit (IC). The demodulator and modulator can also be separate components. In the incoming path, the demodulator strips away the RF carrier signal leaving a baseband receive audio signal, which is sent from the radio system 615 to the baseband system 620.

If the received signal contains audio information, then baseband system 620 decodes the signal and converts it to an analog signal. Then the signal is amplified and sent to a speaker. The baseband system 620 also receives analog audio signals from a microphone. These analog audio signals are converted to digital signals and encoded by the baseband system 620. The baseband system 620 also codes the digital signals for transmission and generates a baseband transmit audio signal that is routed to the modulator portion of the radio system 615. The modulator mixes the baseband transmit audio signal with an RF carrier signal generating an RF transmit signal that is routed to the antenna system and may pass through a power amplifier (not shown). The power amplifier amplifies the RF transmit signal and routes it to the antenna system 610 where the signal is switched to the antenna port for transmission.

The baseband system 620 is also communicatively coupled with the processor 560. The central processing unit 560 has access to data storage areas 565 and 570. The central processing unit 560 is preferably configured to execute instructions (i.e., computer programs or software) that can be stored in the memory 565 or the secondary memory 570. Computer programs can also be received from the baseband processor 610 and stored in the data storage area 565 or in secondary memory 570, or executed upon receipt. Such computer programs, when executed, enable the system 550 to perform the various functions of the present invention as previously described. For example, data storage areas 565 may include various software modules (not shown).

Various embodiments may also be implemented primarily in hardware using, for example, components such as application specific integrated circuits (ASICs), or field programmable gate arrays (FPGAs). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, functions, and methods described in connection with the embodiments disclosed herein can be implemented or performed with a general purpose processor, a digital signal processor (DSP), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

Any of the software components described herein may take a variety of forms. For example, a component may be a stand-alone software package, or it may be a software package incorporated as a "tool" in a larger software product. It may be downloadable from a network, for example, a website, as a stand-alone product or as an add-in package for installation in an existing software application. It may also be available as a client-server software application, as a web-enabled software application, and/or as a mobile application.

While certain embodiments have been described above, it will be understood that the embodiments described are by way of example only. Accordingly, the systems and methods described herein should not be limited based on the described embodiments. Rather, the systems and methods described herein should only be limited in light of the claims that follow when taken in conjunction with the above description and accompanying drawings.

What is claimed is:

1. A sensor system comprising:
a sensorarray comprising a plurality of sensing elements, wherein each of the plurality of sensing elements are functionalized with a deposited mixture consisting of hybrid nanostructures and a molecular formulation specifically targeting at least one of a plurality of gases, and wherein each of the plurality of sensing elements comprises a resistance and a capacitance, and wherein at least one resistance and capacitance are altered when the interacting with gaseous chemical compounds;
an analog front-end coupled with the sensor array and configured to detect the alteration in the resistance or capacitance and produce an analog signal indicative thereof, power each of a plurality of sensing channels associated with the plurality of sensing elements, and convert the analog signal to a digital signal, the analog-front end comprising:
an Analog-to-Digital converter (ADC),
a parking circuit, wherein the parking circuit is configured to provide a constant voltage to any number of connected sensing channels simultaneously, and limit current through each individual sensor channel, and wherein the parking circuit comprises a plurality of switches, and wherein the parking circuit is configured to connect or disconnect any individual sensing channel via the plurality of switches,
a measurement circuit, and
a digital back end coupled with the analog-front end and configured to control the analog front-end, the digital backend comprising: memory comprising, algorithms, models and instructions.

2. The system of claim 1, wherein the instructions are configured to cause a processor to dynamically optimize the analog signal by:
calculating, storing, and setting the gain for each of the plurality of sensor channels wherein each channel is associated with a respective one of the plurality of sensing elements, prior to conversion by the ADC, and
Increasing the signal-to-noise ratio through various oversampling factors.

3. The system of claim 1, wherein the analog-front end is further configured to do at least one of the following: minimize self-heating effects for each of the plurality of sensing elements; maintain operation of each of the plurality of sensing elements in a linear region; minimize power consumption for each of the plurality of sensing element; and prevent short-circuits for each of the plurality of sensing elements.

4. The system of claim 1, wherein the analog-front end is further configured to apply constant voltage across a nanomaterial-based sensor.

5. The system of claim 1, wherein the constant voltage provided by the parking circuit is about 1V.

6. The system of claim 1, wherein the current provided by the parking circuit is limited to about 1 mA.

7. The system of claim 1, wherein the measurement circuit is configured to provide a constant voltage to at least some of the plurality of sensing channels simultaneously and limit the total current through each of the plurality of sensing channels.

8. The system of claim 7, wherein the constant voltage provided by the measurement circuit is about 1V.

9. The system of claim 7, wherein the current provided by the measurement circuit is limited to about 1 mA.

10. The system of claim 7, wherein the measurement circuit comprises either a plurality of switches or a multiplexer configured to connect or disconnect any of the plurality of sensing channels; add an offset to an overall signal associated the plurality of sensing channels; add signals from multiple sensing channels of the plurality of sensing channels to generate a signal of larger amplitude; and add the signals from multiple sensing channels of the plurality of sensing channels to combine the sensing characteristics in a single measurement.

11. The measurement circuit of claim 1, further configured to isolate the sensing channels of the plurality of sensing channels that are being measured from a gain stage, and a data acquisition stage as well as from the sensing channels of the plurality of sensing channels connected to the parking circuit.

12. The measurement circuit of claim 1, further comprising one or more gain stages, wherein each of the one or more gain stages comprise:
   a current mirror, wherein gain is implemented in the current mirror with various mirroring ratios;
   a transimpedance amplifier, configured to converting the current into a voltage;
   a set of selectable resistances for converting the current into a voltage, applying gain to the conversion of current to voltage; and
   a secondary gain stage, comprising an operational amplifier.

13. The system of claim 12, wherein a spacing of selectable gain settings is pre-selected and optimized for a range of each of the plurality of sensing element.

14. The system of claim 13, wherein the spacing of selectable gain settings is geometrically spaced.

15. The system of claim 1, further comprising a make before break circuit, configured to minimize a transient load on a sensing element when the sensing element is being switched from the parking circuit to the measurement circuit and vice versa.

16. A sensor system comprising:
   a sensor array comprising a plurality of sensing elements, wherein each of the plurality of sensing elements are functionalized with a deposited mixture consisting of hybrid nanostructures and a molecular formulation specifically targeting at least one of a plurality of gases, and wherein each of the plurality of sensing elements comprises a resistance and a capacitance, and wherein at least one resistance and capacitance are altered when the interacting with gaseous chemical compounds;
   an analog front-end coupled with the sensor array and configured to detect the alteration in the resistance or capacitance and produce an analog signal indicative thereof, power each of a plurality of sensing channels associated with the plurality of sensing elements, and convert the analog signal to a digital signal, the analog-front end comprising:
   an Analog-to-Digital converter (ADC)
   a parking circuit,
   a measurement circuit, and
   a digital back end coupled with the analog-front end and configured to control the analog front-end, the digital backend comprising: memory comprising, algorithms, models and instructions; and
   one or more gain stages, wherein each of the one or more gain stages comprise:
     a current mirror, wherein gain is implemented in the current mirror with various mirroring ratios,
     a transimpedance amplifier, configured to convert a current of the current mirror into a voltage,
     a set of selectable resistances for converting the current into a the voltage, applying gain to the conversion of current to voltage, and
     a secondary gain stage, comprising an operational amplifier.

17. The system of claim 16, wherein a spacing of selectable gain settings is pre-selected and optimized for a range of each of the plurality of sensing elements.

18. The system of claim 17, wherein the spacing of selectable gain settings is geometrically spaced.

19. The system of claim 16, further comprising a make before break circuit, configured to minimize a transient load on a sensing element when the sensing element is being switched from the parking circuit to the measurement circuit and vice versa.

* * * * *